(12) United States Patent
Tojo et al.

(10) Patent No.: US 11,602,263 B2
(45) Date of Patent: Mar. 14, 2023

(54) INSERTION SYSTEM, METHOD AND COMPUTER-READABLE STORAGE MEDIUM FOR DISPLAYING ATTENTION STATE INFORMATION OVER PLURALITY OF TIMES

(71) Applicant: OLYMPUS CORPORATION, Tokyo (JP)

(72) Inventors: Ryo Tojo, Tokyo (JP); Hiromasa Fujita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 990 days.

(21) Appl. No.: 16/382,454

(22) Filed: Apr. 12, 2019

(65) Prior Publication Data
US 2019/0231444 A1    Aug. 1, 2019

Related U.S. Application Data

(63) Continuation of application No. PCT/JP2016/080245, filed on Oct. 12, 2016.

(51) Int. Cl.
*A61B 1/005*    (2006.01)
*A61B 34/20*    (2016.01)
(Continued)

(52) U.S. Cl.
CPC .............. *A61B 1/009* (2022.02); *A61B 1/00* (2013.01); *A61B 1/00006* (2013.01);
(Continued)

(58) Field of Classification Search
CPC ....... A61B 34/20; A61B 1/00; A61B 1/00006; A61B 1/00045; A61B 1/00147;
(Continued)

(56) References Cited

U.S. PATENT DOCUMENTS

| | | |
|---|---|---|
| 2003/0055317 A1 | 3/2003 | Taniguchi et al. |
| 2005/0010082 A1 | 1/2005 | Nishimura et al. |

(Continued)

FOREIGN PATENT DOCUMENTS

| | | |
|---|---|---|
| CN | 1713848 A | 12/2005 |
| CN | 101534699 A | 9/2009 |

(Continued)

OTHER PUBLICATIONS

English translation of International Preliminary Report on Patentability dated Apr. 25, 2019, together with the Written Opinion received in International Application No. PCT/JP2016/080245.

(Continued)

*Primary Examiner* — Sean D Mattson
(74) *Attorney, Agent, or Firm* — Scully, Scott, Murphy & Presser, P.C.

(57) ABSTRACT

An insertion system having a processor including hardware, configured to: determine, for each of a plurality of times, one or more positions of an insertion section configured to be inserted into an insertion subject; determine, for the each of the plurality of times, state of the insertion section relative to the insertion subject based on the one or more positions for the each of the plurality of times; determine, for the each of the plurality of times, whether an attention state of the insertion section that restricts insertion of the insertion section into the insertion subject has occurred, based on the state of the insertion section relative to the insertion subject determined; and control a monitor to display attention state information indicating the one or more positions of the insertion section at which the occurrence of the attention state of the insertion section is determined over the plurality of times.

19 Claims, 15 Drawing Sheets

(51) Int. Cl.
*A61B 1/00* (2006.01)
*A61B 5/06* (2006.01)
*A61B 1/04* (2006.01)

(52) U.S. Cl.
CPC ...... *A61B 1/00045* (2013.01); *A61B 1/00148* (2022.02); *A61B 5/061* (2013.01); *A61B 5/062* (2013.01); *A61B 34/20* (2016.02); *A61B 1/04* (2013.01); *A61B 2034/2051* (2016.02); *A61B 2034/2074* (2016.02)

(58) Field of Classification Search
CPC ....... A61B 1/04; A61B 1/00009; A61B 1/009; A61B 1/0005; A61B 1/00055; A61B 5/061; A61B 5/062; A61B 5/746; A61B 2034/2051; A61B 2034/2074; A61B 2034/2061; A61B 2090/372; A61B 2090/502
See application file for complete search history.

(56) References Cited

U.S. PATENT DOCUMENTS

| | | | |
|---|---|---|---|
| 2005/0228221 A1* | 10/2005 | Hirakawa | A61B 1/00055 600/101 |
| 2006/0015011 A1 | 1/2006 | Hasegawa et al. | |
| 2009/0221869 A1 | 9/2009 | Tanaka | |
| 2015/0099925 A1 | 4/2015 | Davidson et al. | |
| 2015/0099926 A1* | 4/2015 | Davidson | A61B 1/00052 600/103 |
| 2015/0216391 A1* | 8/2015 | Fujita | A61B 1/00004 600/117 |
| 2017/0112353 A1 | 4/2017 | Ikemoto et al. | |

FOREIGN PATENT DOCUMENTS

| | | | | |
|---|---|---|---|---|
| CN | 106068092 A | 11/2016 | | |
| EP | 1 437 083 A1 | 7/2004 | | |
| EP | 1 504 712 A1 | 2/2005 | | |
| EP | 1 566 140 A1 | 8/2005 | | |
| EP | 2 082 678 A1 | 7/2009 | | |
| JP | 2003-093328 A | 4/2003 | | |
| JP | 2004-167010 A | 6/2004 | | |
| JP | 2004-358095 A | 12/2004 | | |
| JP | 2006-288752 A | 10/2006 | | |
| JP | 2008-136628 A | 6/2008 | | |
| JP | 4274854 B2 * | 6/2009 | ......... | A61B 1/00009 |
| JP | 2011-087793 A | 5/2011 | | |
| JP | 2015-112429 A | 6/2015 | | |
| JP | 2016-154588 A | 9/2016 | | |
| WO | 2003/026497 A1 | 4/2003 | | |
| WO | 2004/039249 A1 | 5/2004 | | |
| WO | 2004/045397 A1 | 6/2004 | | |
| WO | 2008/059636 A1 | 5/2008 | | |
| WO | 2016/136442 A1 | 9/2016 | | |

OTHER PUBLICATIONS

International Search Report dated Dec. 20, 2016 issued in International Application No. PCT/JP2016/080245.

* cited by examiner

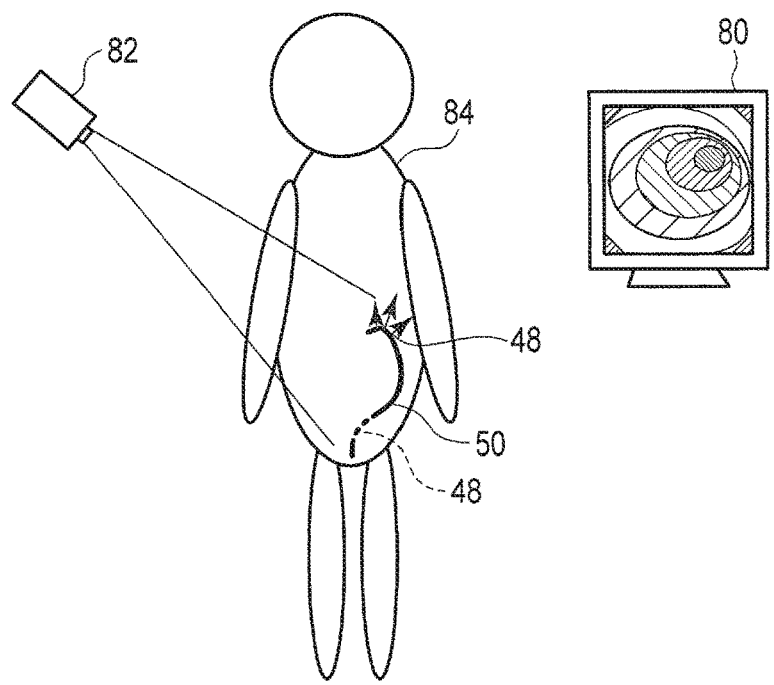

FIG. 20

| [SELECTION OF OUTPUT INFORMATION] | | | [SETTING OF DETECTION SENSITIVITY] | | |
|---|---|---|---|---|---|
| SHAPE | ON | OFF | | | |
| ATTENTION STATE INFORMATION | ON | OFF | | | |
|   EXTENSION INFORMATION | ON | OFF | HIGH | MEDIUM | LOW |
|   BUCKLING INFORMATION | ON | OFF | HIGH | MEDIUM | LOW |
|   LOOP | ON | OFF | HIGH | MEDIUM | LOW |
|   PRESSING FORCE | ON | OFF | HIGH | MEDIUM | LOW |
| [SELECTION OF OUTPUT DEVICE] | | | [SETTING OF OUTPUT SIZE] | | |
| OUTPUT | ON | OFF | | | |
|   MONITOR | ON | OFF | LARGE | MEDIUM | SMALL |
|   SPEAKER | ON | OFF | LARGE | MEDIUM | SMALL |
|   VIBRATION | ON | OFF | LARGE | MEDIUM | SMALL |
|   FLAVOR | ON | OFF | LARGE | MEDIUM | SMALL |

FIG. 21

| [SELECTION OF OUTPUT INFORMATION] | | | [SETTING OF DETECTION SENSITIVITY] | | |
|---|---|---|---|---|---|
| SHAPE | ON | OFF | | | |
| ATTENTION STATE INFORMATION | ON | OFF | | | |
|   EXTENSION INFORMATION | ON | OFF | HIGH | MEDIUM | LOW |
|   BUCKLING INFORMATION | ON | OFF | HIGH | MEDIUM | LOW |
|   LOOP | ON | OFF | HIGH | MEDIUM | LOW |
|   PRESSING FORCE | ON | OFF | HIGH | MEDIUM | LOW |
| RECOMMENDED OPERATION INFORMATION | ON | OFF | | | |
| LESION DETECTION RESULT | ON | OFF | | | |

| [SELECTION OF OUTPUT DEVICE] | | | [SETTING OF OUTPUT SIZE] | | |
|---|---|---|---|---|---|
| OUTPUT | ON | OFF | | | |
|   MONITOR | ON | OFF | LARGE | MEDIUM | SMALL |
|   SPEAKER | ON | OFF | LARGE | MEDIUM | SMALL |
|   VIBRATION | ON | OFF | LARGE | MEDIUM | SMALL |
|   FLAVOR | ON | OFF | LARGE | MEDIUM | SMALL |

18A

F I G. 25

INSERTION SYSTEM, METHOD AND COMPUTER-READABLE STORAGE MEDIUM FOR DISPLAYING ATTENTION STATE INFORMATION OVER PLURALITY OF TIMES

CROSS-REFERENCE TO RELATED APPLICATIONS

This application is a Continuation Application of PCT Application No. PCT/JP2016/080245, filed Oct. 12, 2016, the entire contents of which are incorporated herein by reference.

BACKGROUND

1. Field of the Invention

The present invention relates to an insertion system including a tubular insertion section to be inserted into an insertion object.

2. Description of the Related Art

For example, U.S. Patent Application Publication No. 2003/0055317 discloses a technique of detecting the shape of an insertion section by magnetic shape detection using a coil, and further detecting a specific shape of the insertion section such as a loop shape to send an alert to the operator according to the detected shape.

SUMMARY

According to an embodiment, there is provided an insertion system comprising: a processor comprising hardware, wherein the processor is configured to: determine, for each of a plurality of times, one or more positions of an insertion section configured to be inserted into an insertion subject; determine, for the each of the plurality of times, a state of the insertion section relative to the insertion subject based on the one or more positions of the insertion section determined for the each of the plurality of times; determine, for the each of the plurality of times, whether an attention state of the insertion section that restricts insertion of the insertion section into the insertion subject has occurred, based on the state of the insertion section relative to the insertion subject determined; and control a monitor to display attention state information indicating the one or more positions of the insertion section at which the occurrence of the attention state of the insertion section is determined over the plurality of times.

According to another embodiment, there is provided a method comprising: determining, for each of a plurality of times, one or more positions of an insertion section configured to be inserted into an insertion subject; determining, for the each of the plurality of times, a state of the insertion section relative to the insertion subject based on the one or more positions of the insertion section determined for the each of the plurality of times; determining, for the each of the plurality of times, whether an attention state of the insertion section that restricts insertion of the insertion section into the insertion subject has occurred, based on the state of the insertion section relative to the insertion subject determined; and controlling a monitor to display attention state information indicating the one or more positions of the insertion section at which the occurrence of the attention state of the insertion section is determined over the plurality of times.

According to another embodiment, there is provided a non-transitory computer-readable storage medium configured to store instructions that cause a computer to at least perform: determining, for each of a plurality of times, one or more positions of an insertion section configured to be inserted into an insertion subject; determining, for the each of the plurality of times, a state of the insertion section relative to the insertion subject based on the one or more positions of the insertion section determined for the each of the plurality of times; determining, for the each of the plurality of times, whether an attention state of the insertion section that restricts insertion of the insertion section into the insertion subject has occurred, based on the state of the insertion section relative to the insertion subject determined; and controlling a monitor to display attention state information indicating the one or more positions of the insertion section at which the occurrence of the attention state of the insertion section is determined over the plurality of times.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 20 is a diagram showing another example of the output device.

FIG. 21 is a diagram showing an example of display for output selection.

FIG. 25 is a diagram showing an example of display for output selection in the second embodiment.

DETAILED DESCRIPTION

Hereinafter, embodiments for implementing the present invention will be described with reference to the drawings.

In the following description, a medical endoscope, specifically, a flexible endoscope for the large intestine is taken as an example. However, the present invention can be generically applied as long as it is an insertion system including an insertion section to be inserted into an insertion object and at least part thereof has flexibility. In addition, the insertion object is not limited to a human body but may be an animal or other structure. For example, the present invention can be applied not only to medical endoscopes (upper gastrointestinal tract endoscope, large intestine endoscope, ultrasonic endoscope, cystoscope, pyeloscope, bronchoscope, etc.) but also to catheters, as well as manipulators, industrial endoscopes, treatment tools, etc.

First Embodiment

Figure 1:
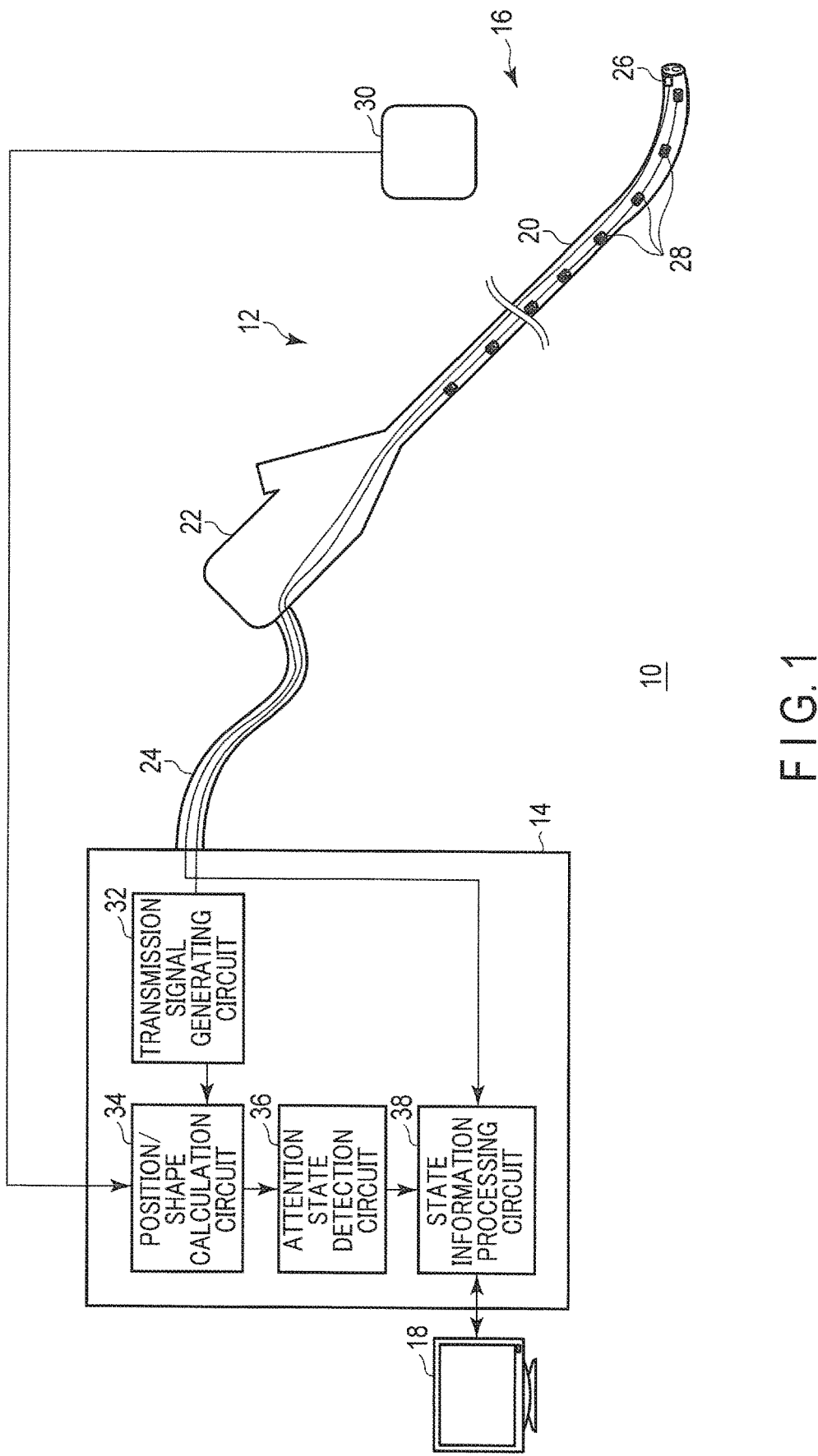
FIG. 1 is a schematic diagram showing the configuration of an endoscope system as an insertion system according to a first embodiment of the present invention.

As shown in FIG. 1, an endoscope system 10 as a tubular insertion system according to a first embodiment of the present invention includes an endoscopic scope 12, an endoscope system main body 14, a magnetic position detection sensor 16, and a monitor 18.

The endoscopic scope 12 includes an elongated insertion section 20 which is a bending member, an operation section 22 connected to a proximal end portion of the insertion section 20, and a connection cable 24 for connecting the operation section 22 and the endoscope system main body 14. The endoscopic scope 12 is a tubular insertion device for inserting the tubular insertion section 20 into an insertion object, which in this embodiment is a human body, and more specifically the large intestinal lumen.

The insertion section 20 has, from the distal end side of the insertion section 20 to the proximal end side thereof, a distal end rigid portion, an operation bending portion that bends, and a flexible tube portion. Here, the distal end rigid portion is the distal end portion of the insertion section 20 and the distal end portion of the endoscopic scope 12 and is a rigid member. An imaging device 26 (e.g., a CCD) as a camera is incorporated in the distal end rigid portion. An operator such as a doctor can bend the operation bending portion in a desired direction by operating an unillustrated operation knob provided on the operation section 22. The flexible tube portion has desired flexibility and is bent by an external force. The operator inserts the insertion section 20 from an entrance of the insertion object, in this embodiment, from the anus, and observes the interior of the large intestinal lumen by the imaging device 26 provided at the distal end.

Also, in the insertion section 20, a transmission coil 28, which is a part of the magnetic position detection sensor 16, is arranged. Depending on the application, a single transmission coil 28 may be used, but in order to detect the shape of the insertion section 20, usually a plurality of transmission coils 28 are arranged at different positions in the longitudinal direction of the insertion section 20. When a current of electricity to be described later flows from the endoscope system main body 14, these transmission coils 28 generate a magnetic field signal.

A magnetic field signal generated by these transmission coils 28 is detected by a reception antenna 30 which is a part of the magnetic position detecting sensor 16. The reception antenna 30, which is composed of a plurality of unillustrated receiving coils, detects the magnetic field signal generated by the transmission coil 28. The intensity information of the detected magnetic field is input in the endoscope system main body 14. In the endoscope system main body 14, in order to calculate the position of each transmission coil 28 based on the intensity of the detected magnetic field, the reception antenna 30 is fixed at a position near the insertion object, specifically fixed so as not to move with respect to a room or a bed.

On the other hand, the endoscope system main body 14 includes a transmission signal generation circuit 32, a position/shape calculation circuit 34, an attention state detection circuit 36, and a state information processing circuit 38. The transmission signal generation circuit 32, position/shape calculation circuit 34, attention state detection circuit 36, and state information processing circuit 38 may be respectively configured in the form of a separate hardware circuit or may be integrated together with other constituent members into one hardware circuit. Furthermore, a software program to cause a computer processor to function as the transmission signal generation circuit 32, position/shape calculation circuit 34, attention state detection circuit 36, and/or state information processing circuit 38 may be prepared in an unillustrated memory, and the processor may be configured to execute at least one function of each of them by executing the program.

The transmission signal generation circuit 32 is a part of the magnetic position detection sensor 16. The transmission signal generation circuit 32 generates signals for generating a magnetic field from each transmission coil 28 of the endoscopic scope 12, e.g., a sinusoidal current. The generated signals are output to each of the plurality of transmission coils 28 in the order determined for each of the plurality of transmission coils 28, for example, in order from a transmission coil 28 on the distal end side of the insertion section 20. In FIG. 1, only one wiring is illustrated for the sake of simplification of the drawing, but two wirings for each transmission coil 28 are inserted into the inside of the endoscopic scope 12 from the transmission signal generation circuit 32. Furthermore, the transmission signal generation circuit 32 supplies, to the position/shape calculation circuit 34, output timing information indicating to which transmission coil 28 the signal is being output at the present moment.

The position/shape calculation circuit 34 functions as an insertion section state detection circuit that detects state information which is at least a part of state of the insertion section 20. The position/shape calculation circuit 34 is connected to the magnetic position detection sensor 16. That is, the position/shape calculation circuit 34 is connected to the reception antenna 30 and the transmission signal generation circuit 32. The position/shape calculation circuit 34 is also connected to the attention state detection circuit 36. The position/shape calculation circuit 34 calculates positional information of each transmission coil 28 based on the intensity information of the magnetic field input from the reception antenna 30 and the output timing information supplied from the transmission signal generation circuit 32. Then, the position/shape calculation circuit 34 acquires the obtained positional information of the plurality of transmission coils 28, as the shape information of the insertion section 20. In addition, the position/shape calculation circuit 34 may be configured to interpolate the positional information of the plurality of transmission coils 28 by spline processing and to acquire the result as shape information, as the occasion demands. As described above, the positional information and/or the shape information indicates the state of a portion of the insertion section 20 where the transmission coils 28 are arranged, namely, the state of at least a part of the insertion section 20. Hereinafter, the positional information and/or shape information is referred to as state information. The position/shape calculation circuit 34 outputs the thus obtained state information to the attention state detection circuit 36.

The attention state detection circuit 36 has a threshold relating to the state information of the insertion section 20, compares the state information of the insertion section 20 input from the position/shape calculation circuit 34 with the threshold, and detects the occurrence of an attention state, which is a state preventing insertion of the insertion section 20, and a position where the attention state has occurred, based on the comparison result.

The attention state detection circuit 36 detects, for example, the following states as the attention state.

Extension: Detecting a state where the intestine has been stretched and the distal end of the insertion section 20 does not move further relative to the current position or the distal end returns to the current position, even if the operator performs an insertion operation in a state where the operation bending portion on the distal end side of the insertion section 20 is bent (the imaging device 26 is taking a picture of the interior of the large intestinal lumen).

Deflection (Buckling): Detecting a state where the middle portion of the insertion section 20 is unintentionally deflected, the force for inserting the insertion section 20 escapes from the deflected portion in a direction different from the insertion direction, and the distal end does not move further.

Loop: Detecting a state where the insertion section 20 has a loop shape. If necessary, the type of loop (α loop, γ loop, or N loop) and the overlapping state (relation of vertical positions) of the insertion section 20 are also detected.

Pressing force: Detecting a force applied by the insertion section 20 to the intestine. In the present embodiment, a force applied to the insertion section 20, i.e., a force applied to the intestine is detected from the already known rigidity of the insertion section 20 and a change in the shape of the insertion section 20.

The attention state detection circuit 36 may have a plurality of thresholds for the same attention state and calculate the degree of attention of an attention state.

Figure 2:
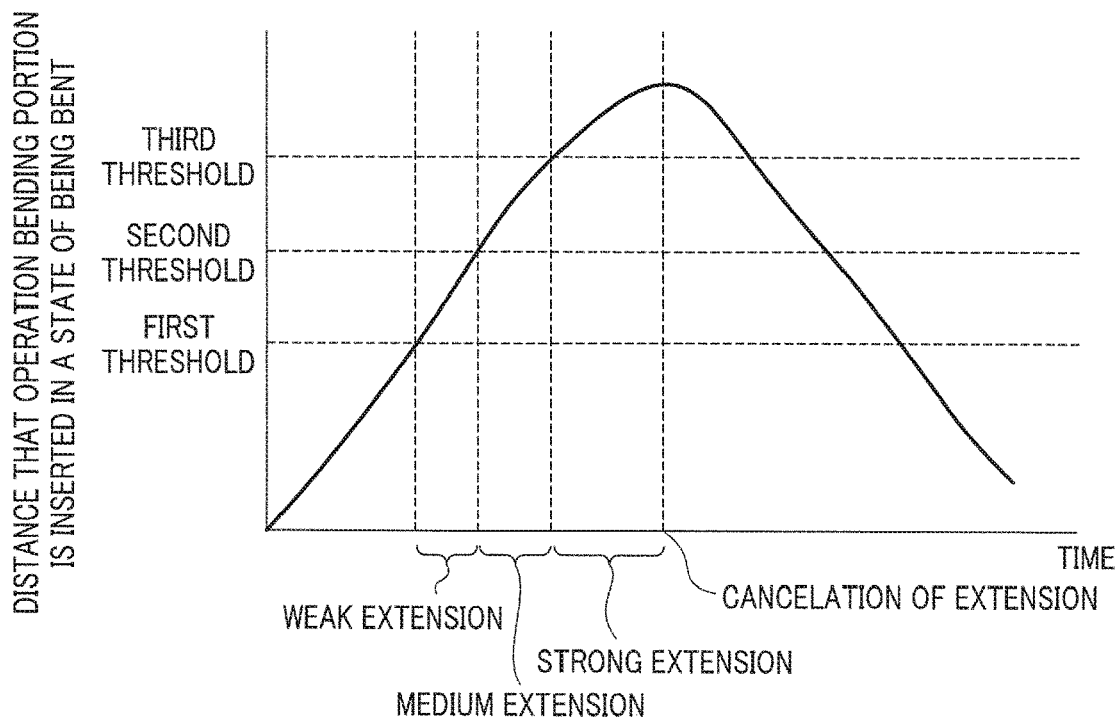
FIG. 2 is a diagram showing an example of a plurality of thresholds for detecting extension, which is one of attention states.

FIG. 2 shows an example in which an extension state is detected with a plurality of thresholds. First to third thresholds are provided for the distance that the operation bending portion is inserted in a state of being bent, which is one parameter for detecting extension. The distance in this case is determined, for example, based on the positional information of the transmission coil 28 near the apex of the bend. In this embodiment, it is assumed that the attention state detection circuit has a total of three thresholds from first to third. If the distance is less than the first threshold, the attention state detection circuit 36 determines that extension has not occurred. If the distance exceeds the first threshold, the attention state detection circuit 36 determines that weak extension is occurring. Likewise, if the distance exceeds the second threshold, it determines that medium extension is occurring, and if the distance exceeds the third threshold, the attention state detection circuit 36 determines that strong extension is occurring. Also, from the tendency that the distance increases with time, when the tendency reverses in a direction that the distance is decreasing, the attention state detection circuit 36 determines that the extension is canceled.

Figure 3:
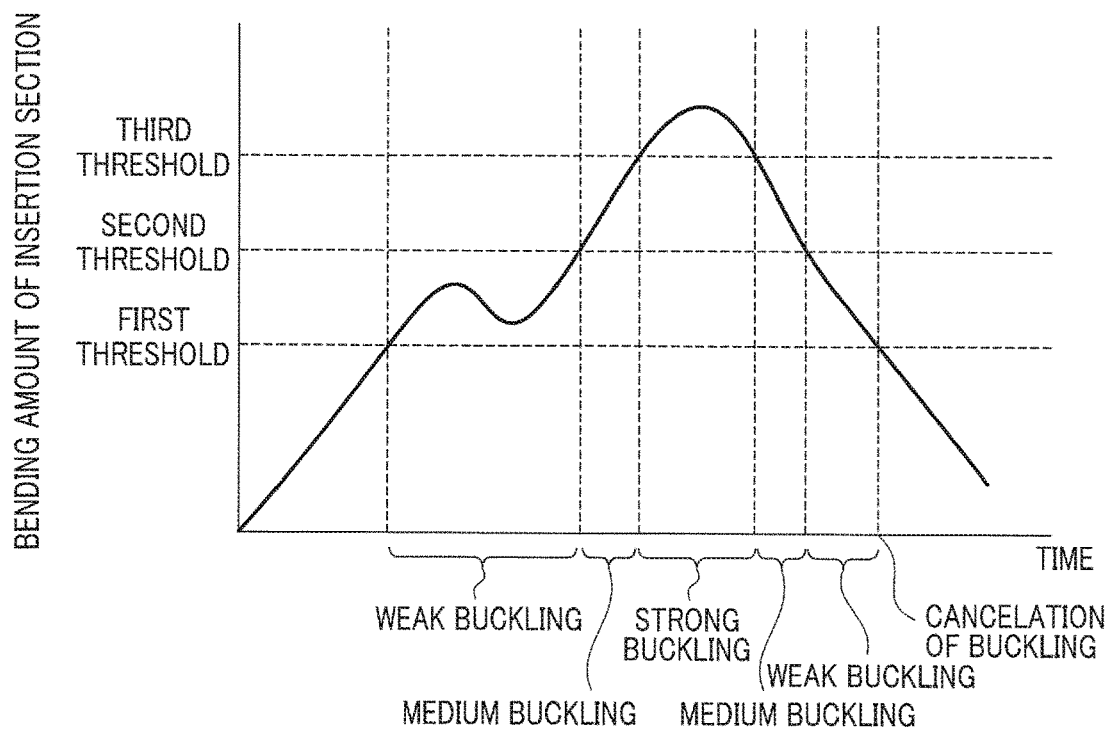
FIG. 3 is a diagram showing an example of a plurality of thresholds for detecting buckling, which is a different attention state.

Furthermore, FIG. 3 shows an example in which buckling is detected with a plurality of thresholds. For this buckling detection, a total of three thresholds from the first to the third are provided for the bending amount of the insertion section 20. The bending amount is determined, for example, from positional information of a plurality of adjacent transmission coils 28, i.e., the shape information. If the bending amount is less than the first threshold, the attention state detection circuit 36 determines that no buckling is occurring; if the bending amount exceeds the first threshold, it determines that weak buckling is occurring; if the bending amount exceeds the second threshold, it determines that medium buckling is occurring; and if the bending amount exceeds the third threshold, it determines that strong buckling is occurring. When the bending amount exceeds the third threshold and thereafter becomes equal to or less than the third threshold, the attention state detection circuit 36 determines that the buckling is medium buckling, and thereafter, if the bending amount is equal to or less than the second threshold, the attention state detection circuit 36 determines that the buckling is weak buckling. Then, if the bending amount further becomes equal to or less than the first threshold, the attention state detection circuit 36 determines that the buckling is canceled.

The attention state detection circuit 36 outputs the state information input from the position/shape calculation circuit 34, the detected attention state and the detected position, and if necessary, the degree of attention, to the state information processing circuit 38.

The state information processing circuit 38 performs image processing for displaying and outputting the state information input from the attention state detection circuit 36 on the monitor 18. Also, based on the attention state and the position (and the degree of attention) detected by the attention state detection circuit 36, the state information processing circuit 38 performs image processing for outputting attention state information expressing the content of the attention state to the monitor 18 for display thereon. Furthermore, the state information processing circuit 38 receives an image signal from the imaging device 26 that images the interior of the large intestinal lumen, performs general image processing for the image signal, and generates an endoscopic image. Then, the state information processing circuit 38 generates a display image including the state information, the attention state information, and the endoscopic image, and outputs the display image to the monitor 18.

The monitor 18, which is one of the output devices, is, for example, a liquid crystal display in which an input interface such as a touch panel is provided on a display screen. The monitor 18 displays an endoscopic image and displays state information and attention state information. By viewing the display screen of the monitor 18, the operator can observe the interior of the large intestinal lumen as well as know the state of the insertion section 20. Various setting screens of the endoscope system 10 can be displayed on the monitor 18 to perform various settings by touch panel operation. Of course, instead of providing a touch panel equipped monitor 18, a dedicated input device may be separately provided.

Although not specifically illustrated in the drawings, the endoscope system 10 includes an air supply mechanism for discharging a gas such as air or carbon dioxide gas from the distal end of the insertion section 20 into the large intestinal lumen, an air suction mechanism for sucking the gas in the large intestinal lumen from the distal end of the insertion section 20, a water absorption mechanism for absorbing liquid in the large intestinal lumen from the distal end of the insertion section 20, and an illumination mechanism for illuminating the field of view of the imaging device 26. The endoscopic scope 12 has a forceps channel for inserting a treatment tool such as forceps from the operation section 22 side through to the distal end portion of the insertion section 20.

Figure 4:
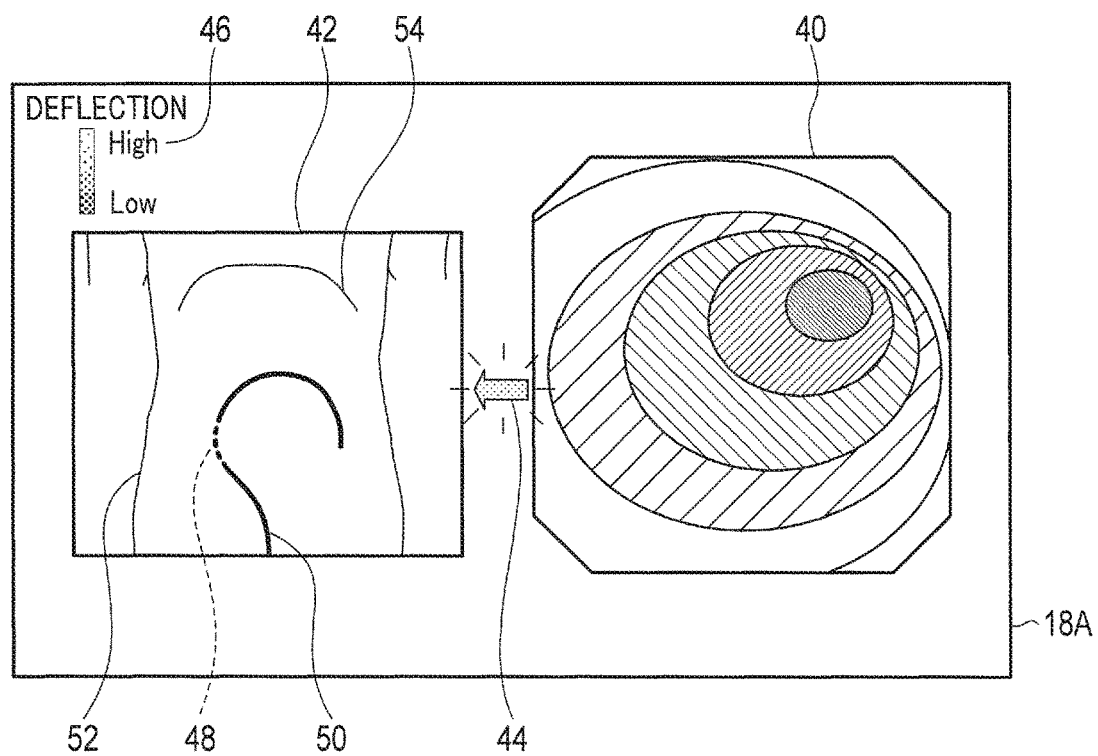
FIG. 4 is a diagram showing an example of display on a monitor.

FIG. 4 is a diagram showing an example of display of an endoscopic image, state information and attention state information on a touch panel-equipped display screen 18A of a monitor 18.

In the present embodiment, a configuration is explained in which an endoscopic image and both the state information and attention state information are displayed on one monitor 18 as an output device; however, it goes without saying that the monitor 18 as an output device for displaying and outputting the state information and the attention state information may be configured to be separate from a display as a display device that displays an endoscopic image. In this case, apart from the state information processing circuit 38, a dedicated image processor may be provided which performs general image processing for an image signal from the imaging device 26 to generate an endoscopic image.

The touch panel-equipped display screen 18A displays an endoscopic image 40, a detailed state information display area 42, an attention state notification indicator 44, and a state information explanation area 46. On the display screen, the endoscopic image 40 and the detailed state information display area 42 are displayed side by side as windows, and the attention state notification indicator 44 is displayed therebetween. The state information explanation area 46 is displayed at the upper left of the detailed state information display area 42. The state information processing circuit 38 executes image processing for performing such display, generates a display image, and supplies the display image to the monitor 18, so that the monitor 18 displays the display image. Hereinafter, details of this display image will be described.

The detailed state information display area 42 is an area for displaying attention state information 48 in association with a position where the attention state has occurred. Specifically, in the detailed state information display area 42, the attention state information 48 is displayed in association with state information 50 which is a shape of the insertion section 20 detected by the position/shape calculation section 34 using the magnetic position detection sensor 16. This association will be described later with reference to FIGS. 5 to 9. Furthermore, in the detailed state information display area 42, the positional relationship of the state information 50 relative to the human body can be determined by depicting a shape 52 of the human body as an insertion object and a medical region 54 of the human body, e.g., the epigastric fossa or diaphragm, relative to the shape 52 of the human body.

Next, a method of displaying the attention state information 48 in the detailed state information display area 42 will be described.

Figure 5:
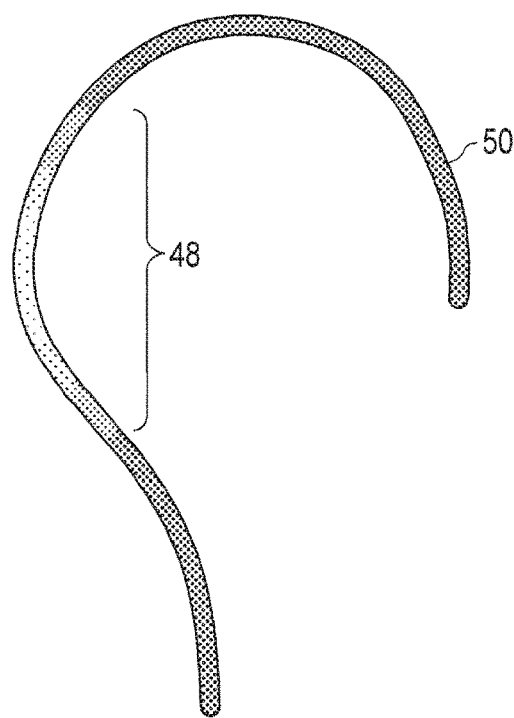
FIG. 5 is a diagram showing a display example of attention state information in a detailed state information display area.

FIG. 5 shows an example of displaying attention state information 48 by changing the color of a scope in which the attention state is occurring in the shape of the insertion section 20, as state information 50. For example, the color of a portion where deflection has occurred is changed; furthermore, the color is changed from yellow to orange and to red according to the degree of attention of deflection calculated by the attention state detection circuit 36 by comparing the state information with a plurality of thresholds, i.e., the bending amount of the insertion section 20 where deflection is occurring.

With this configuration, the operator can know a place where the deflection has occurred in the insertion section 20 and the deflection amount. It goes without saying that the density, transparency, or brightness in the scope where an attention state is occurring may be changed, instead of the color, for portions other than the scope where the attention state is occurring.

Figure 6:
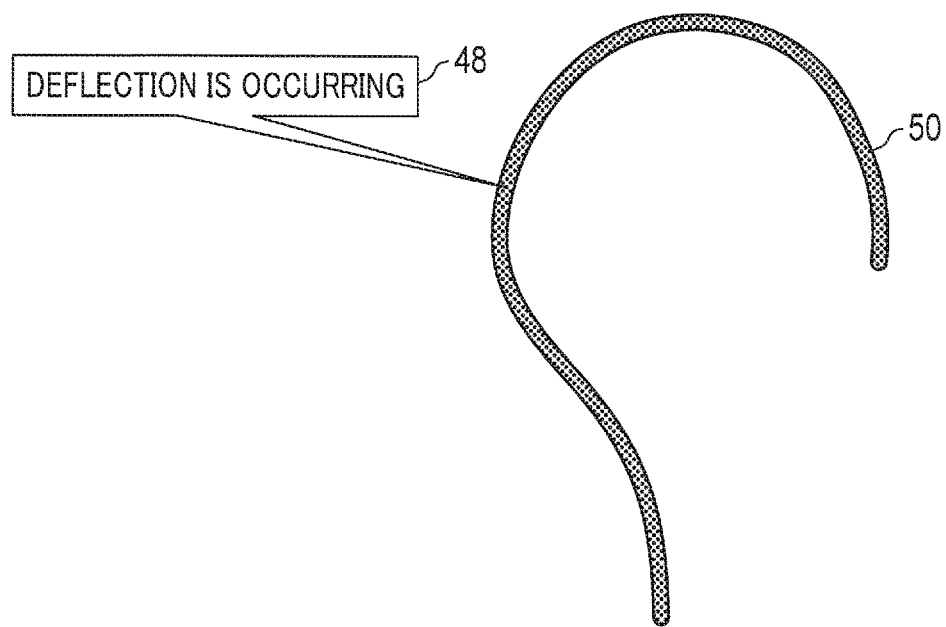
FIG. 6 is a diagram showing another display example of attention state information in the detailed state information display area.

FIG. 6 is an example of displaying attention state information 48 as characters (in this example, "deflection has occurred") explaining what kind of attention state has occurred, while indicating a position where the attention state is occurring in the shape of the insertion section 20 which is state information 50.

Figure 7:
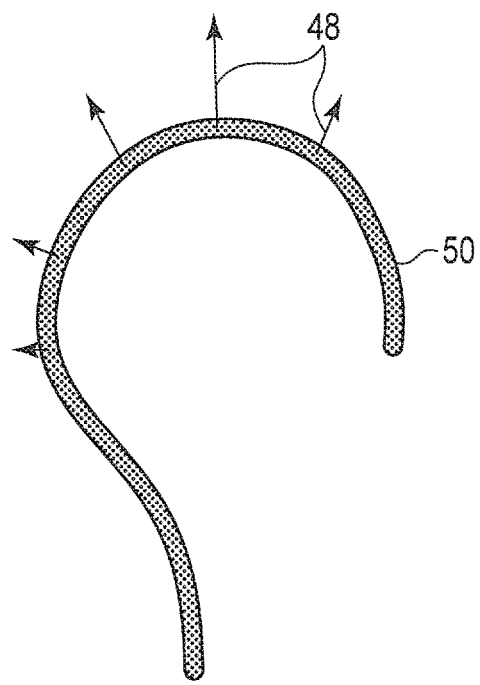
FIG. 7 is a diagram showing another display example of attention state information in the detailed state information display area.

FIG. 7 is an example of displaying attention state information 48 as arrows in the shape of the insertion section 20 which is state information 50. For example, based on a detection result of the pressing force by the position/shape calculation circuit 34, the magnitude of the force applied to the intestine by the insertion section 20 is indicated by the size and length of the arrows. Also, the direction in which the force is applied is displayed in the direction of each arrow. In this case, the color may be changed according to the magnitude of the force. By displaying the force applied to the intestine with an arrow or arrows, the operator can visually and easily ascertain the magnitude of the force applied to the intestine, and easily judge whether to continue the insertion or to perform another operation. Since this does not add an unreasonable force to the intestines, the safety will be improved. In addition, since the person who is an insertion object does not feel pain, the comfort will be improved. It goes without saying that not only arrows but also other figures may be used as long as the attention state can be expressed thereby.

Figure 8:
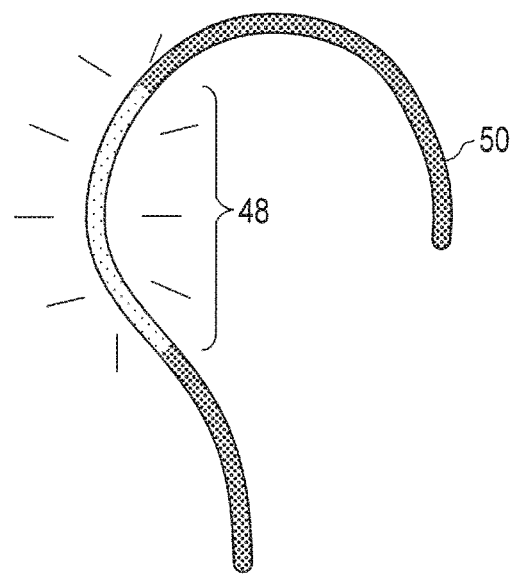
FIG. 8 is a diagram showing another display example of attention state information in the detailed state information display area.

FIG. 8 is an example of displaying the attention state information 48 by blinking a portion where the attention state occurs in the shape of the insertion section 20 which is state information 50. In this case, the blinking speed may be further changed according to the degree of attention.

It goes without saying that in display of the attention state information 48, two or more of such color, density, transparency, brightness, characters, figures, and blinking may be combined.

Figure 9:
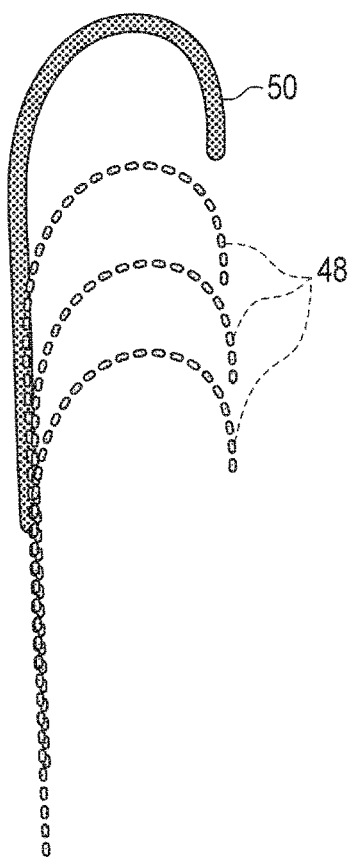
FIG. 9 is a diagram showing another display example of attention state information in the detailed state information display area.

Furthermore, as shown in FIG. 9, when an attention state occurs, the attention state information 48 may be displayed by displaying tracks of the shape of the insertion section 20 which is state information 50. For example, when an extension occurs, tracks are displayed. The tracks of the shape of the insertion section 20 may be displayed by changing the color according to the degree of attention of the extension, i.e., the insertion amount of the insertion section 20 that is inserted, in the state where the extension is occurring. It is possible to compare the shape and position of the past insertion section 20 with those of the present insertion section 20, so it is easy to understand a change in the state of the insertion section 20, and it is possible to know that an extension has occurred.

Such display of the attention state information 48 is erased when the attention state ends; for example, when the insertion section 20 is extracted and the extension state is canceled. Of course, this display erasure timing is not limited thereto, and it may be changed as necessary. For example, even after an extraction operation has been performed in an extension, the attention state information 48 may be displayed continuously for a certain period of time or up to a certain insertion or extraction length of the insertion section 20.

The state information explanation area 46 is a section for displaying an explanation of the attention state information 48 displayed in the detailed state information display area 42. The example of FIG. 4 shows an explanation about color changes of deflection "yellow⇔orange⇔red", i.e., yellow indicates that the deflection amount is small (the degree of deflection is low), and red indicates that the deflection amount is large (the degree of deflection is high). This state information explanation area 46 is not always necessary, and can be omitted, for example, when the explanation on the attention state information 48 is displayed with characters as shown in FIG. 6.

The attention state notification indicator 44 is a section for displaying to urge the operator who is viewing an endoscopic image 40 to see the detailed state information display area 42, when an attention state occurs, that is, when the state of the insertion section 20 is to be notified to the operator. The attention state notification indicator 44 is disposed in the vicinity of the periphery of the endoscopic image 40. Here, the vicinity of the periphery of the endoscopic image 40 indicates a scope that falls within the field of view of the operator when the operator is watching the endoscopic image 40. In the example of FIG. 4, the attention state notification indicator 44 is displayed in the form of an arrow pointing to the detailed state information display area 42 between the endoscopic image 40 and the detailed state information display area 42.

Normally, the operator performs an insertion operation of the insertion section 20 while mainly observing an endoscopic image 40, so it is rare for the operator to see the detailed state information display area 42, for example, during the insertion operation. Therefore, even if only the detailed state information display area 42 is displayed and then attention state information 48 is displayed due to occurrence of an attention state, there are concerns that the operator may not notice the attention state information 48. Therefore, when an attention state occurs, the attention state notification indicator 44 entering the field of view of the operator informs the operator of the occurrence of the attention state, so that the operator can recognize that the attention state has occurred, and the operator can check and confirm the detailed state information display area 42 as necessary. By allowing the operator to recognize an attention state and to know a cause of preventing the insertion, it helps the operator to determine a method of the insertion operation, and the insertability of the insertion section 20 is improved.

Figure 10:
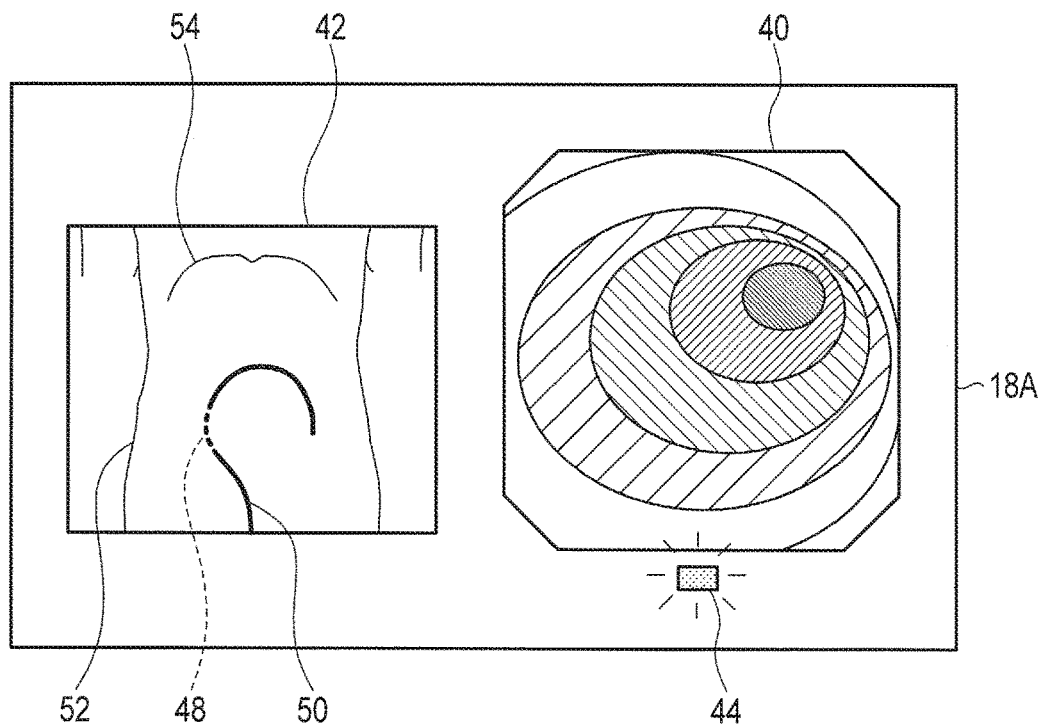
FIG. 10 is a diagram showing another display example of an attention state notification indicator.
Figure 11:
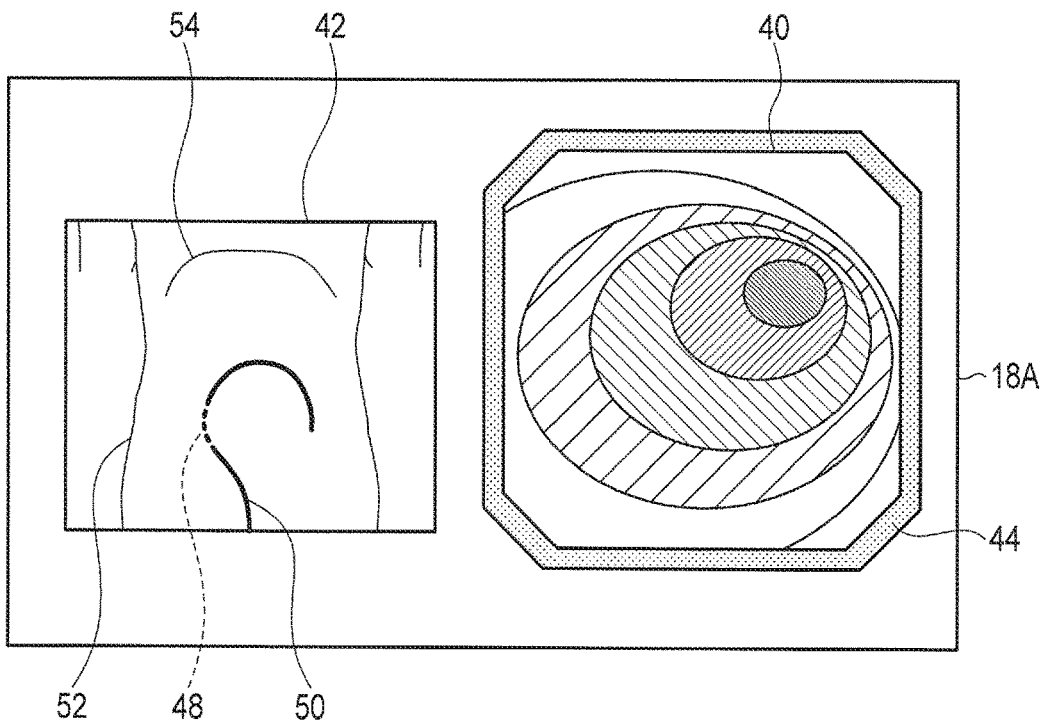
FIG. 11 is a diagram showing another display example of the attention state notification indicator.
Figure 12:
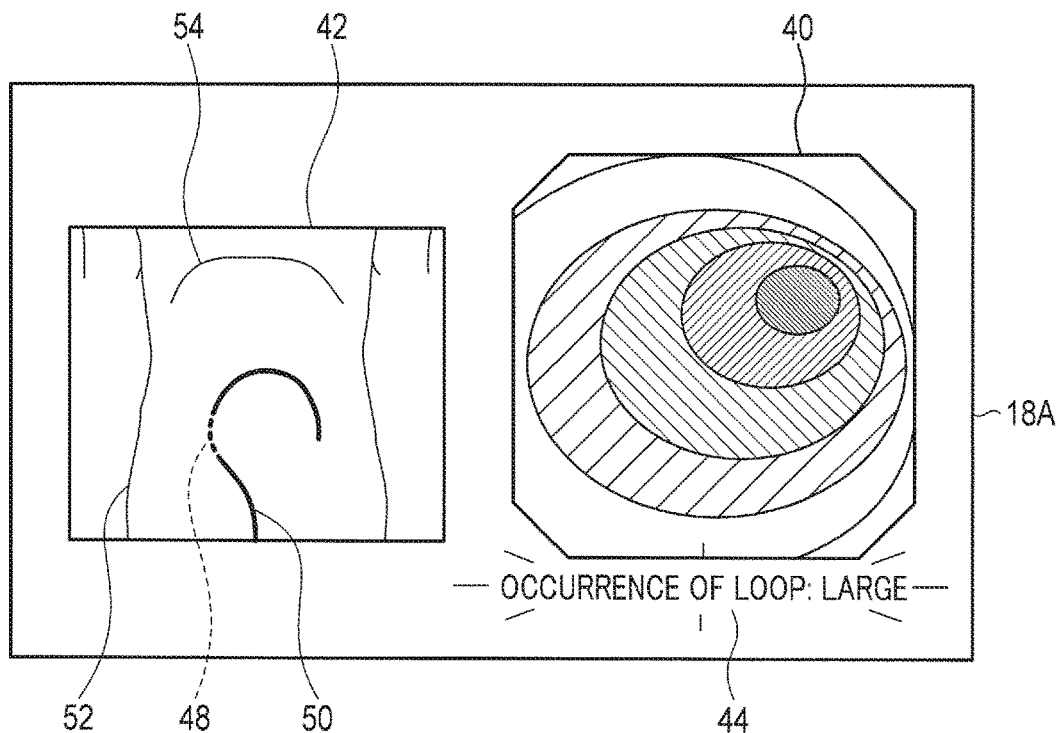
FIG. 12 is a diagram showing another display example of the attention state notification indicator.

If the operator who is watching the endoscopic image 40 can notice that an attention state has occurred, the attention state notification indicator 44 is not limited to the method of lighting up the arrow as shown in FIG. 4. For example, as shown in FIG. 10, the attention state notification unit 44 may be an indication that simulates an LED that lights up in the vicinity of the periphery of an endoscopic image 40, or may change the color of the surroundings of an endoscopic image 40 as shown in FIG. 11, or may indicate an attention state using characters as shown in FIG. 12.

Figure 13:
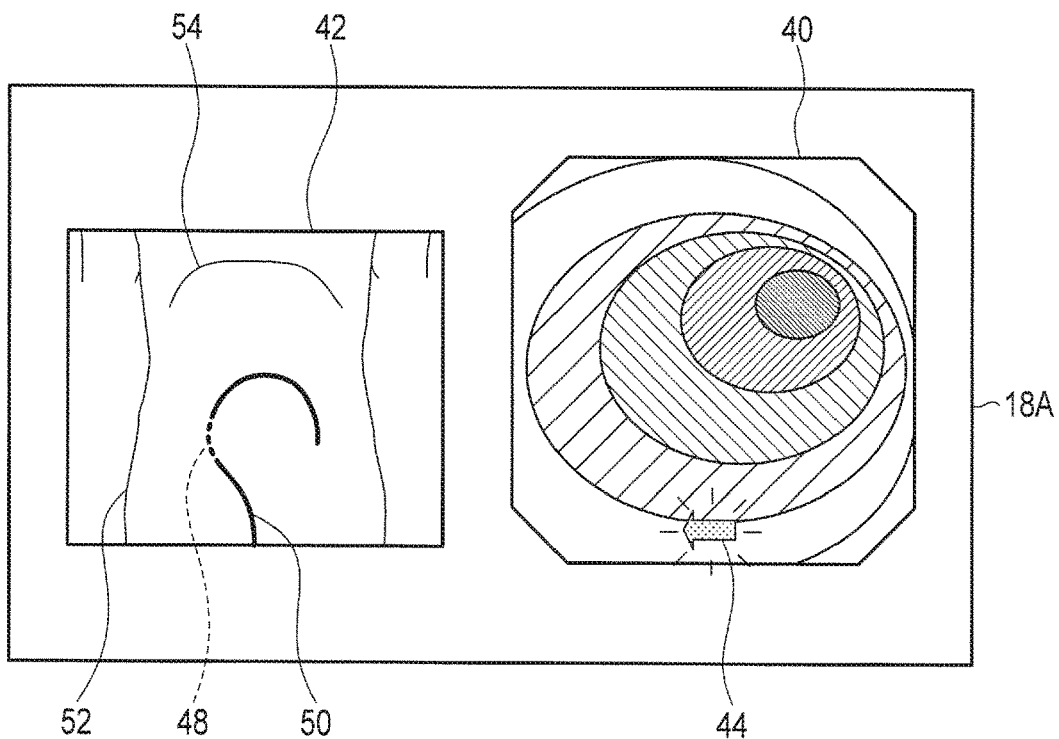
FIG. 13 is a diagram showing another display example of the attention state notification indicator.

In addition, the attention state notification indicator 44 is not limited to being disposed in the vicinity of the periphery of an endoscopic image 40, but as shown in FIG. 13, the attention state notification indicator 44 may be superimposed and displayed on an endoscopic image 40. Also in this case, the attention state notification indicator 44 is not limited to an arrow, but it may be displayed with other figures and characters. The operator normally performs an insertion operation while viewing an endoscopic image 40, and therefore, by displaying the attention state notification indicator 44 in a state of being superimposed on the endoscopic image 40 in this way, the operator can recognize more reliably that an attention state has occurred. In addition, when the attention state notification indicator 44 is superimposed and displayed on an endoscopic image 40, the attention state notification indicator 44 may be semitransparently displayed so that a portion of the endoscopic image 40 cannot be seen due to the presence of the attention state notification indicator 44.

Figure 14:
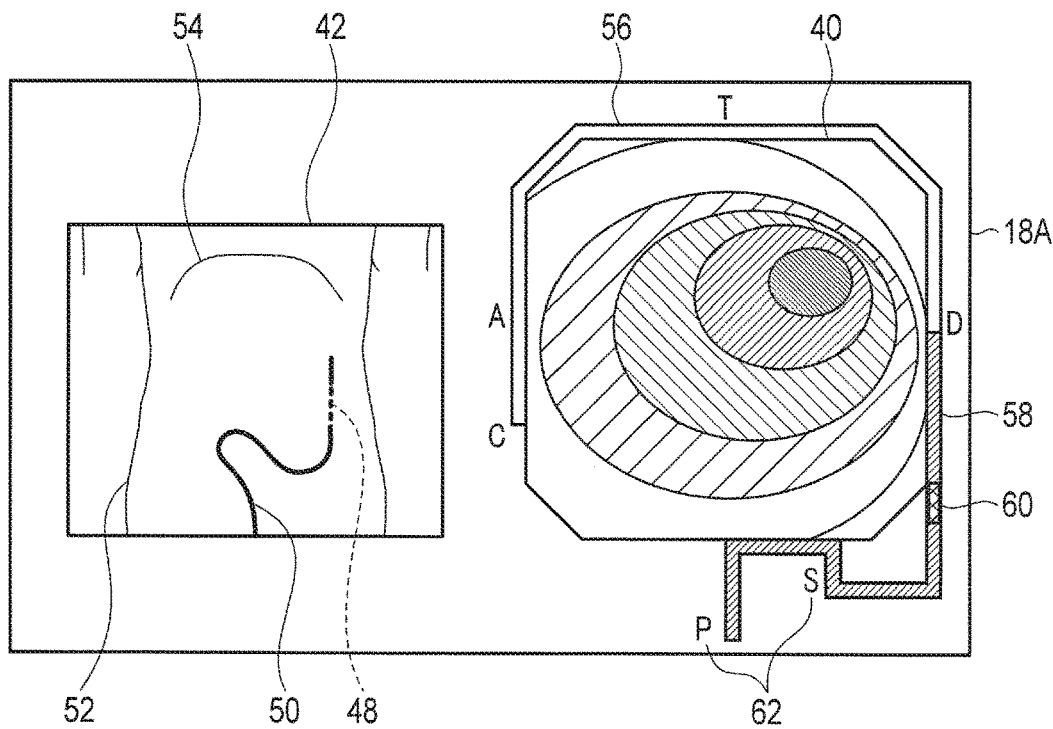
FIG. 14 is a diagram showing an example of an imaging area attention state information indicator.

The attention state information is not limited to being displayed in the detailed state information display area 42. For example, as shown in FIG. 14, apart from the detailed state information display area 42, an imaging area attention state information indicator 56 which simply indicates attention state information in association with the position of the insertion section 20 may be displayed in the periphery of the endoscopic image 40. That is, the state information processing circuit 38 can generate a display image including such an imaging area attention state information indicator 56 in addition to the endoscopic image 40, attention state information 48, and state information 50, and can output the display image to a touch panel-equipped display screen 18A. In the example of FIG. 14, the imaging area attention state information indicator 56 is displayed in a simplified shape depicting the large intestine in the periphery of the endoscopic image 40. Furthermore, the imaging area attention state information indicator 56 may be configured to perform an insertion amount display 58 of the insertion section 20 indicated by color and/or perform an attention state display 60 indicating that an attention state has occurred. At that time, abbreviations 62 of regions (P (Proctodeum), S (Sigmoid colon), D (Descending colon), T (Transverse colon), A (Ascending colon), and C (Cecum)) may be written so that the regions of the large intestine can be ascertained relative to the shape simply depicting the large intestine. In addition to the abbreviations 62, names of the regions may be written or may be indicated in the figure. By displaying the attention state display 60 in a portion of the insertion amount display 58 of the insertion section 20 corresponding to a position in the longitudinal direction of the insertion amount display 58, the operator can know at which position in the insertion section 20 the attention state is occurring.

Figure 15:
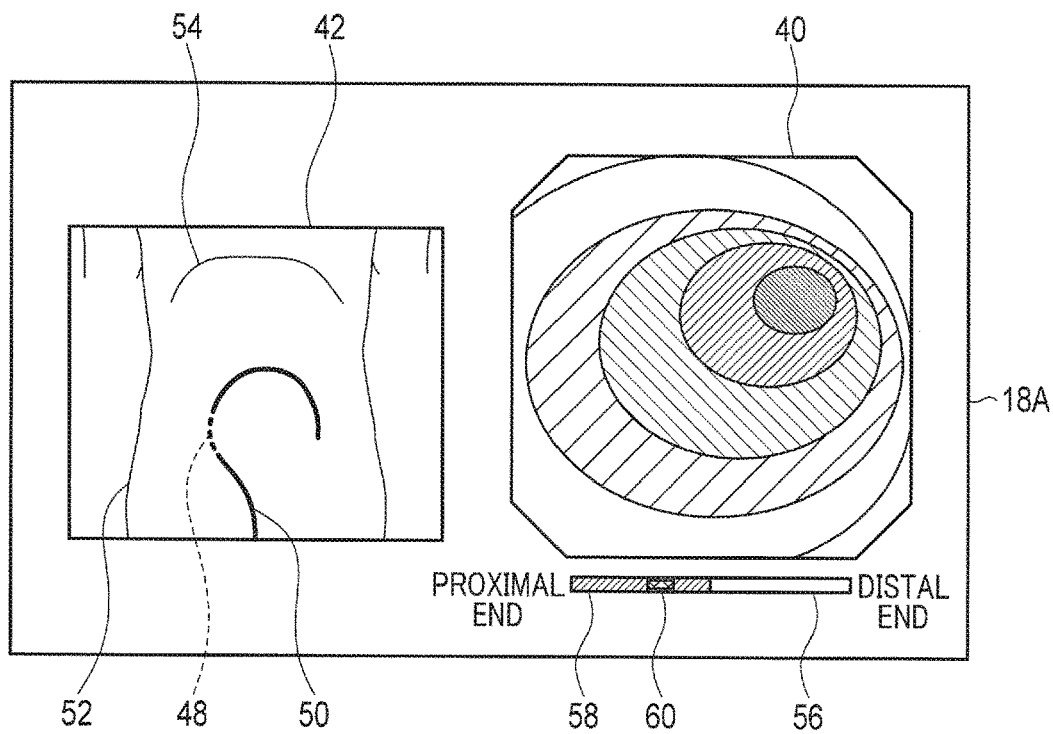
FIG. 15 is a diagram showing another example of the imaging area attention state information indicator.

Of course, the imaging area attention state information indicator 56 is not necessarily required to be formed in a shape that simply depicts the large intestine, and as shown in FIG. 15, it may display the large intestine in a linear graph and perform the insertion amount display 58 and the attention state display 60.

Both the detailed state information display area 42 and the imaging area attention state information indicator 56 may be displayed as necessary, or only one of them may be displayed.

Similarly to the attention state information 48 in the detailed state information display area 42, the color, density, transparency, brightness, characters, figures, and/or blinking of the attention state display 60 in the imaging area attention state information indicator 56 may also be changed according to the degree of attention.

Figure 16:
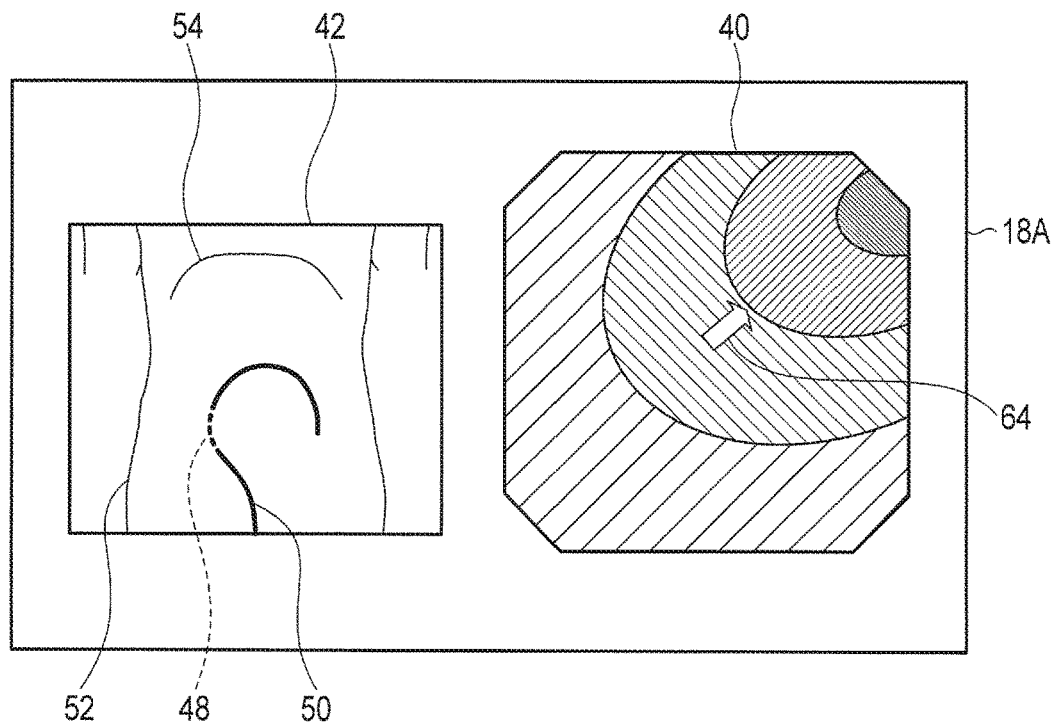
FIG. 16 is a diagram showing an example of a luminal direction indicator.

Furthermore, as attention state information, a luminal direction indicator 64 indicating an extending direction of the large intestinal lumen in an endoscopic image 40 may be displayed as shown in FIG. 16. That is, the state information processing circuit 38 detects the extending direction of the large intestinal lumen by analyzing an image signal captured by the imaging device 26, for example, by determining brightness and darkness. Alternatively, the state information processing circuit 38 detects the extending direction of the large intestinal lumen from the shape of the large intestine and the shape of the insertion section 20, given as vision information, and an insertion amount of the insertion section 20. Based on the detection result, the state information processing circuit 38 can generate a display image including such a luminal direction indicator 64 in addition to the endoscopic image 40, the attention state information 48, and the state information 50 and can output it to the monitor 18. Particularly in a state where the extending direction of the large intestinal lumen is out of the endoscope screen, that is, in a state where the imaging device 26 is imaging the inner wall of the large intestine instead of the inner side thereof, performing the bending operation of the insertion section 20 by the operation section 22 so as to move the insertion section 20 in which direction depends on the operator's sense and past experience. On the other hand, by superimposing and displaying such a lumen direction indicator 64 on an endoscopic image 40, the operator can recognize the direction in which the large intestinal lumen extends, so that the operator can know the direction in which the operation bending portion of the insertion section 20 is to be bent, and therefore, the insertability is improved.

Figure 17:
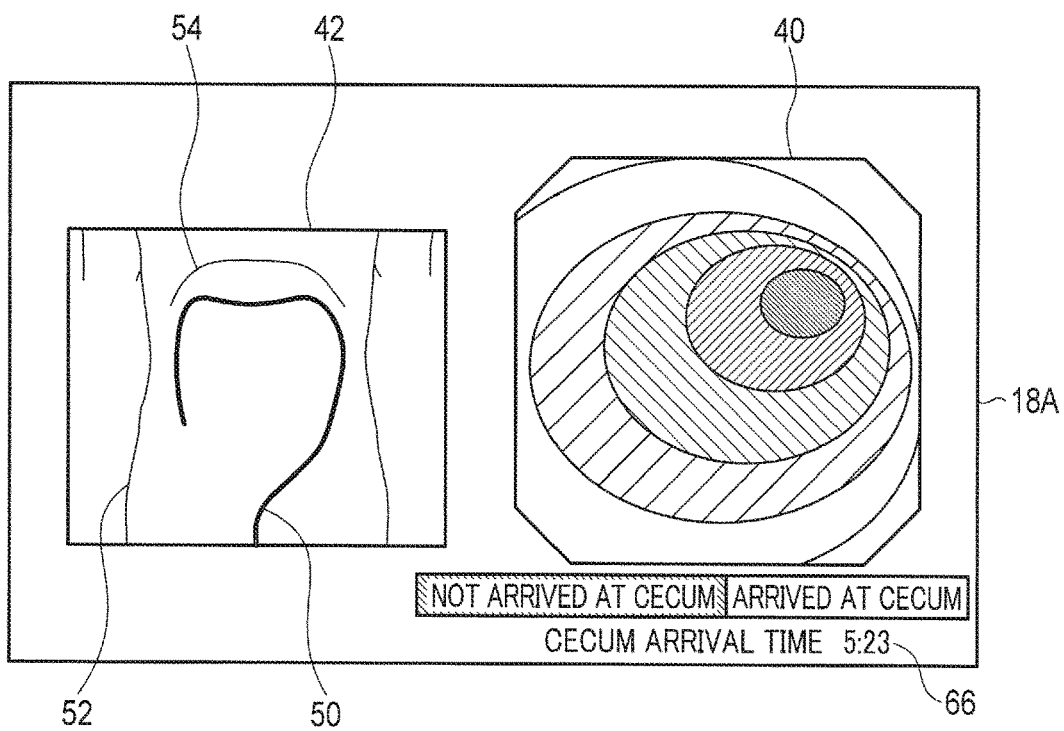
FIG. 17 is a diagram showing an example of a cecum arrival information display area.

Furthermore, as the attention state information, a cecum arrival information display area 66 may be displayed, in which information on a cecum arrival is displayed, as shown in FIG. 17. The information on arrival of the cecum is, for example, whether or not the insertion section 20 has arrived at the cecum, and when the insertion section 20 has arrived at the cecum, the time from the start of insertion to the arrival. That is, the state information processing circuit 38 detects whether or not the insertion section 20 has arrived at the cecum by analyzing an image signal captured by the imaging device 26. Alternatively, the state information processing circuit 38 may presume that the insertion section 20 has arrived at the cecum, from the shape of the large intestine and the shape of the insertion section 20, given as vision information. Based on the detection result, the state information processing circuit 38 generates a display image including such a cecum arrival information display area 66 in addition to the endoscopic image 40, the attention state information 48, and the state information 50, and can output the display image to a monitor 18. Although the cecum is taken as an example, the arrival information is not necessarily limited thereto, and the arrival information to be displayed may be changed appropriately in accordance with a specific region of an insertion object.

Figure 18:
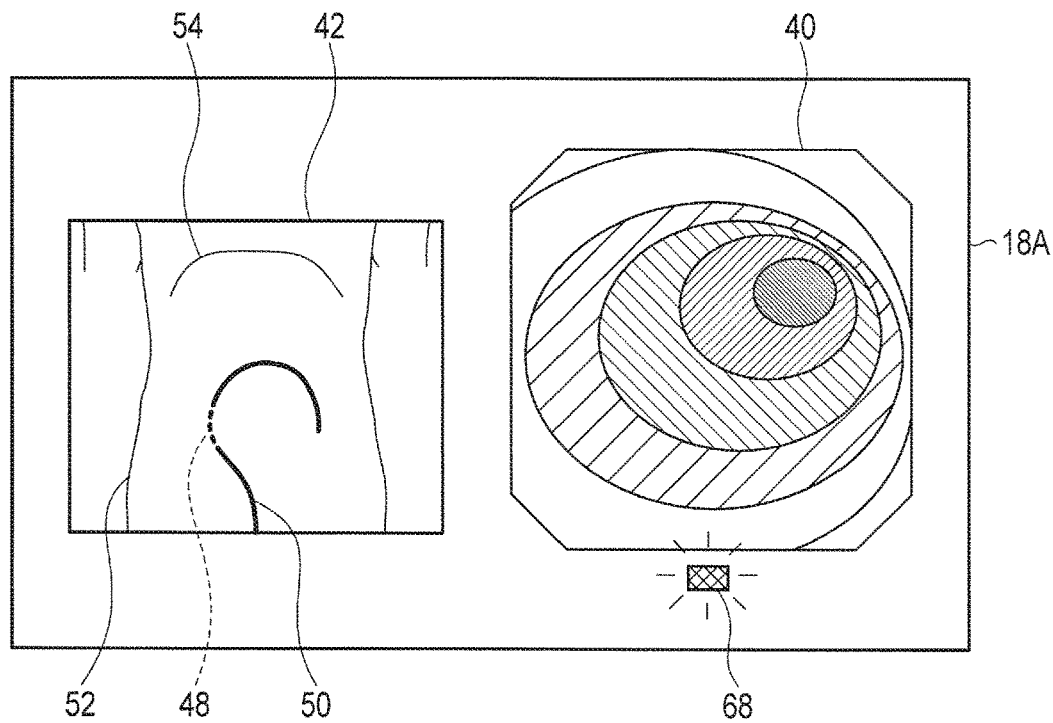
FIG. 18 is a diagram showing an example of a normal state indicator.

Also, as shown in FIG. 18, a normal state indicator 68 may be displayed which indicates that the insertion section 20 is inserted normally, that is, it is in a state where the insertion section 20 is approaching the cecum, or in a state where an excessive load is not applied to the intestine. That is, the attention state detection circuit 36 can further detect a normal insertion state which is a state where the insertion section 20 is normally inserted, and the state information processing circuit 38 can further generate a display image including the normal state display indicator 68 indicating normal insertion state information according to the detection of the normal insertion state and can output it to the monitor 18. With such a normal state display section 68, the operator can recognize that there is no problem with the operation of the endoscopic scope 12.

Furthermore, in addition to displaying the attention state information 48 and the state information 50 on the monitor 18, another output device may be used to convey attention state information and state information to the operator.

Figure 19:
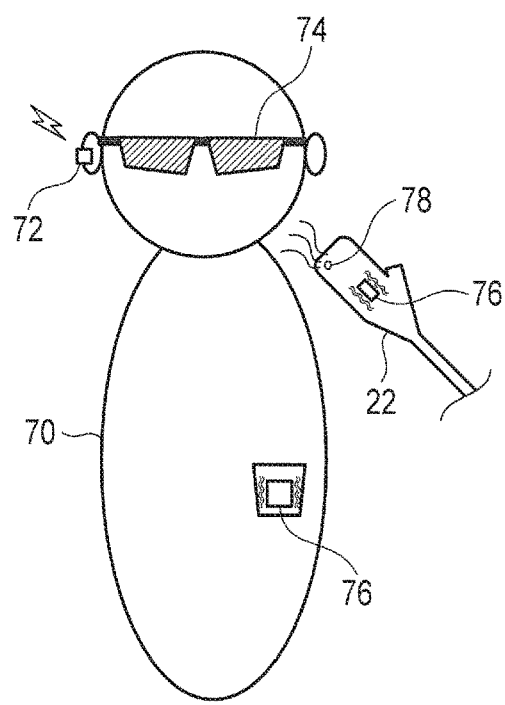
FIG. 19 is a diagram showing various examples of an output device.

As an output device separate from the display device for displaying an endoscopic image 40, for example, as shown in FIG. 19, it is possible to notify an operator 70 of attention state information by sound by using an earphone 72 worn by the operator 70. In this case, the state information processing circuit 38 changes the type and size of sound output from a speaker of the earphone 72 according to the content of an attention state that has occurred and the degree of attention, whereby the operator 70 can easily know what kind of attention state has occurred and to what extent. Although the earphone 72 is used as an example of a sound output, a speaker, etc., placed in a room in which the endoscope system 10 is installed may be used as long as the operator 70 can recognize the sound. Furthermore, attention state information may be conveyed by light or vibration by using an eyeglasses type monitor 74 or a vibration generator 76, which is an example of a wearable terminal worn by the operator 70. Also in this case, the state information processing circuit 38 changes the type and intensity of light and vibration according to the content of an attention state that has occurred and the degree of attention. Furthermore, a vibration generator 76 such as a piezoelectric element or a scent generator 78 may be disposed in the operation section 22 of the endoscopic scope 12 to convey the attention state information by vibration or scent. Also in this case, the state information processing circuit 38 changes the type and intensity of vibration and scent according to the content of an attention state that has occurred and degree of attention.

Furthermore, as shown in FIG. 20, a projector 82 may also be used as an output device separate from a display 80 which is a display device for displaying an endoscopic image 40. In this case, attention state information and state information may be displayed on the body of a patient 84 as an insertion object by projection mapping. Thus, the position of the insertion section 20 and the position of the attention state, relative to the patient 84, can be easily understood.

The operator may change the settings relating to the output of the shape which is the attention state information 48 and the state information 50. For example, as shown in FIG. 21, a setting screen relating to the output is displayed on a touch panel-equipped display screen 18A of the monitor 18, and output information is selected and designated by a touch panel which is an input interface. In this example, ON/OFF designation can be selected to display the shape and the attention state information 48 as output information. Furthermore, as for the attention state information 48, extension, buckling, etc., can be individually ON/OFF-designated. Furthermore, sensitivity settings may be provided for the attention state information 48 so that the operator can set the sensitivity to determine whether to make it easy to detect the attention state information 48 or whether to make it difficult to detect the attention state information 48.

Furthermore, as shown in FIGS. 19 and 20, when there are a plurality of output devices, it may be configured to select an output device or output devices to be used. Also, the magnitude of an output may be set according to an output device used. For example, in the case of the monitor 18, the size of the display can be changed; in the case of a speaker of the earphone 72, the magnitude of sound can be changed; in the case of vibration of the vibration generator 76, the intensity of vibration can be changed, and in the case of the scent generator 78, the intensity of scent can be changed.

Output information and an output device may be selected through another input interface such as a mouse, instead of the touch panel of the touch panel-equipped display screen 18A of the monitor 18. Furthermore, instead of the setting screen displayed on the monitor 18, output information and an output device may be selected through an input interface in which an operator can input, such as a physical switch.

Such a selection designation result by the input interface is input in the state information processing circuit 38, and the state information processing circuit 38 performs processing for outputting the ON-designated output information, supplies the processed output information to an ON-designated output device, and causes the output device to output it. Also, the state information processing circuit 38 outputs the detection sensitivity about the ON-designated output information to the attention state detection circuit 36, and the attention state detection circuit 36 adjusts a threshold of the state information in accordance with the designation of the detection sensitivity.

As described above, the endoscope system 10 as the insertion system according to the first embodiment includes a position/shape calculation circuit 34 as an insertion section state detection circuit that detects state information of at least a part of the insertion section 20; an attention state detection circuit 36 that has a threshold of state information and detects an attention state including at least an attention state relating to an insertion operation of the insertion section 20 based on a comparison between the state information and the threshold; a state information processing circuit 38 that performs processing for outputting attention state information expressing the content of the attention state based on the detection result of the attention state detection circuit 36; and an output device such as the monitor 18, earphone 72, eyeglass type monitor 74, vibration generator 76, scent generator 78, projector 82, etc., which output information including attention state information 48 processed by the state information processing circuit 38.

Therefore, since the insertion section is configured to detect at least an attention state relating to an insertion operation based on a comparison between state information and a threshold, and to perform processing for outputting attention state information expressing the content of the attention state based on the detection result, it is possible to provide an insertion system capable of presenting at least an attention state relating to an insertion operation to the operator 70.

By allowing the operator 70 to recognize at least attention state information relating to an insertion operation of the insertion section 20, the operator 70 can know the cause of preventing the insertion, for example, extension or deflection, which is one type of attention state information, which helps the operator to determine a method of the insertion operation, and the insertability is improved. By allowing the operator to know the pressing force (the force applied to the intestine), which is one type of attention state information, the operator 70 can easily, visually know the magnitude of the force given to the intestine, making it easy to determine whether to continue or interrupt the insertion, or to perform another operation. Since an unreasonable force is not applied to the intestine, the safety will be improved. In addition, since the patient 84 does not feel pain, the comfort is improved.

In this embodiment, the position/shape calculation circuit 34 detects the position of the insertion section 20, which is one of the state information, the attention state detection circuit 36 further detects the position of the insertion section 20 at which an attention state has occurred, the state information processing circuit 38 performs processing for displaying the detailed state information display area 42 that displays attention state information 48 in association with the position of the insertion section 20 on the monitor 18 or the projector 82 as an output device, based on the detection result of the attention state detection circuit 36.

Therefore, by adopting the configuration as shown in this embodiment, it is possible to present attention state information 48 to the operator 70 in an easy-to-understand manner.

Then, in this case, the state information processing circuit 38 performs, based on the attention state information, processing for displaying, on the monitor 18 and the projector 82, the detailed state information display area 42 which displays the attention state information 48 by changing at least one of color, characters, figures, and presence or absence of blinking at a position where an attention state of the insertion section 20 displayed on the detailed state information display area 42 has occurred.

As described above, by changing the color of the shape of the insertion section 20, displaying a figure such as an arrow, or displaying characters, based on the attention state information, it is possible to provide the operator 70 with state information of the insertion section 20 and attention state information 48 in an easy-to-understand manner. That is, by displaying the shape of the insertion section 20 and changing the display state of the position of the insertion section 20 where the attention state occurs, the operator 70 can ascertain the position on the insertion section 20 where the attention state occurs.

Alternatively, the state information 50 detected by the position/shape calculation circuit 34 includes at least apart of the shape of the insertion section 20, and the state information processing circuit 38 performs processing for displaying, on the monitor 18 and the projector 82, the detailed state information display area 42 in which attention state information 48 is displayed as a track of a shape change in the at least a part of the shape of the insertion section 20, based on the attention state information.

As described above, by displaying the track of the insertion section 20 based on the attention state information, it is possible to provide the operator 70 with the state information of the insertion section 20 and the attention state information 48 in an easy-to-understand manner.

Alternatively, the state information 50 detected by the position/shape calculation circuit 34 includes at least a part of the shape of the insertion section 20, and the state information processing circuit 38 may be configured to further perform processing for displaying, on the monitor 18, the detailed state information display area 42 in which the shape of the insertion section 20 is simultaneously displayed with the shape of an insertion object such as a human body shape 52.

With this configuration, the positional relationship of the insertion section 20 relative to the shape of the insertion object can be determined.

In particular, the insertion object includes a human body such as a patient 84, and the state information processing circuit 38 performs processing for displaying, on the monitor 18, the detailed state information display area 42 in which a medical region 54 of the human body with respect to the human body shape 52, for example, the epigastric fossa and the diaphragm, is depicted.

With this configuration, the positional relationship of the insertion section 20 relative to the human body of the state information 50 can be determined.

The insertion section 20 includes an imaging device 26 as a camera, and an image of the interior of an insertion object captured by the imaging device 26, such as an endoscopic image 40, is displayed on the monitor 18, or the insertion system further includes a display 80 as a display device, and the image is displayed on the display 80.

That is, the image of the interior of the insertion object captured by the imaging device 26 can be displayed together with the attention state information 48.

In this case, the state information processing circuit 38 may be configured to further perform processing for displaying, on the monitor 18 or the display 80, the imaging area attention state information indicator 56 which indicates the attention state information 48 by changing at least one of the color, characters, figures, and presence or absence of blinking on an image captured by the imaging device 26 or near the image.

As described above, by displaying the attention state information 48 in the vicinity of the periphery of an image captured by the imaging device 26, such as the endoscopic image 40, or on the image, the operator 70 can know the attention state information 48 while paying attention to the image captured by the imaging device 26 or without largely looking aside from the image.

The attention state detection circuit 36 may be configured to have a plurality of thresholds of state information, calculate the degree of attention of an attention state based on a comparison between the state information and the plurality of thresholds, and the state information processing circuit 38 may be configured to change the display of the attention state information 48 based on the degree of attention.

With this configuration, the operator 70 can execute an operation related to the insertion in consideration of the degree of the state information.

Alternatively, the position/shape calculation circuit 34 may be configured to detect the position of the insertion section 20, which is one of the state information, the attention state detection circuit 36 may be configured to detect the position of the insertion section 20 where an attention state has occurred, and the state information processing circuit 38 may be configured to perform processing for displaying, on the monitor 18 or the display 80, the imaging area attention state information indicator 56 which indicates an attention state display 60 indicating an attention state information in association with the position of the insertion section 20.

With this configuration, the operator 70 can ascertain the position on the insertion section 20 where the attention state is occurring.

Alternatively, the attention state information may further include information indicating the extending direction of an insertion object in an image captured by the imaging device 26, and the state information processing circuit 38 may be configured to further perform processing for displaying, on the monitor 18 or the display 80, the attention state information including information indicating the extending direction of the insertion object as a luminal direction indicator 64, based on the detection result of the attention state detection circuit 36 and the image captured by the imaging device 26.

With this configuration, the operator 70 becomes to know the direction in which the large intestinal lumen extends, whereby the operator 70 becomes to know the direction in which the operation bending portion of the insertion section 20 is to be bent, and therefore, the insertability is improved.

In addition, the insertion section 20 may include an imaging device 26 as a camera, and an image of an interior of an insertion object captured by the imaging device 26 such as an endoscopic image 40 may be displayed on the monitor 18, or the insertion system may further include a display 80 as a display device to display the image on the display 80. The state information processing circuit 38 may perform processing for displaying the detailed state information display area 42 on the monitor 18 independently of the image captured by the imaging device 26, or processing for displaying, on a monitor 18, separate from the display 80, the image captured by the imaging device 26 displayed on the display 80. The state information processing circuit 38 may be configured to further perform processing for displaying, on the monitor 18 or the display 80, an attention state notification indicator 44 indicating that the attention state information 48 is displayed in the detailed state information display area 42 on the image captured by the imaging device 26 or near the image.

The operator 70 needs to pay attention mainly to the endoscopic image 40; however, the attention state notification indicator 44 as described above enables the operator 70 to recognize that an attention state is occurring even when paying attention to the endoscopic image 40, and to ascertain the details of the attention state on the detailed state information display area 42 where necessary.

The attention state detection circuit 36 may be configured to further detect a normal insertion state which is a state where the insertion section 20 is normally inserted, and the state information processing circuit 38 may be configured to further perform processing for outputting normal insertion state information, for example, as a normal state indicator 68, to an output device, based on a detection result of the attention state detection circuit 36.

With such a normal state display section 68, the operator 70 can recognize that there is no problem with the insertion operation of the insertion section 20.

Furthermore, the state information processing circuit 38 preferably further performs processing for outputting, to an output device, an explanation of the attention state information 48 that has been output to the output device, as shown in the state information explanation area 46.

With this configuration, the operator 70 can easily ascertain the content of the attention state information 48.

The position/shape calculation circuit 34 may include a magnetic position detection sensor 16.

This makes it possible to detect the shape of the insertion section as state information.

The insertion system may further include an input interface, such as a touch panel of a touch panel-equipped display screen 18A of the monitor 18, a mouse, and a physical switch, for designating ON/OFF of an output of the attention state information 48, and the state information processing circuit 38 may be configured to perform processing for outputting the attention state information 48 in accordance with an ON designation of the output of the attention state information 48.

With this configuration, the operator 70 can switch between presence and absence of an output of attention state information in accordance with the proficiency or the preference of the insertion operation of the operator 70.

The insertion system may be an endoscope system 10 including an imaging device 26 as a camera.

Alternatively, the insertion system may be a large intestine endoscope system including an imaging device 26 as a camera. In this case, attention state information may include at least one of whether or not the insertion section 20 has arrived at the cecum and the cecum arrival time, which is displayed as a cecum arrival information display area 66 on the monitor 18 which is an output device.

With this configuration, it becomes possible to present, to the operator 70, whether or not the insertion section has arrived at the cecum or the cecum arrival time, which is important information in a large intestine endoscope system.

Second Embodiment

Next, a second embodiment of the present invention will be described. In the following, the same reference numerals are given to the same constituent members as those in the first embodiment, the explanation thereof will be omitted, and only portions different from the first embodiment will be described.

Figure 22:
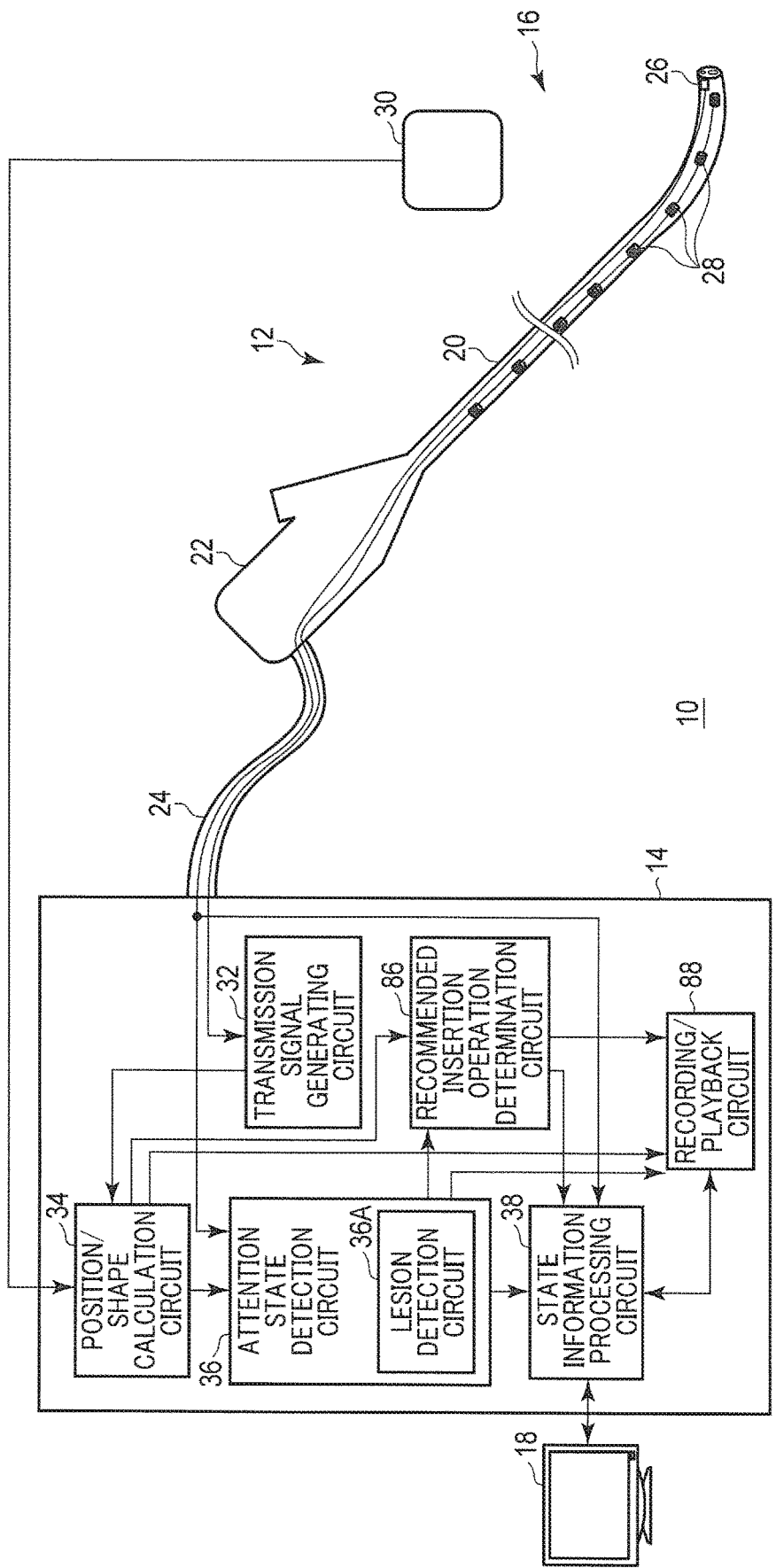
FIG. 22 is a schematic diagram showing the configuration of an endoscope system as an insertion system according to a second embodiment of the present invention.

As shown in FIG. 22, an endoscope system 10 as a tubular insertion system according to a second embodiment of the present invention includes, inside an endoscope system main body 14, a recommended insertion operation determination circuit 86 and a recording/playback circuit 88 in addition to the transmission signal generation circuit 32, the position/shape calculation circuit 34, the attention state detection circuit 36, and the state information processing circuit 38. The attention state detection circuit 36 includes a lesion detection circuit 36A.

Similarly to the transmission signal generation circuit 32, position/shape calculation circuit 34, attention state detection circuit 36, and state information processing circuit 38, the recommended insertion operation determination circuit 86 and the recording/playback circuit 88 may be respectively configured in the form of a separate hardware circuit or may be integrated together with other constituent members into one hardware circuit. Furthermore, a software program to cause a computer processor to function as the transmission signal generation circuit 32, position/shape calculation circuit 34, attention state detection circuit 36, state information processing circuit 38, recommended insertion operation determination circuit 86 and/or recording/playback circuit 88 may be prepared in an unillustrated memory, and the processor may be configured to execute at least one function of each of them by executing the program.

The recommended insertion operation determination circuit 86 determines recommended insertion operation information, which is a method of a recommended insertion operation, based on at least one of the shape calculated by the position/shape calculation circuit 34 and the attention state information 48 detected by the attention state detection circuit 36, and which is for advancing the insertion or improving the safety. The recommended insertion operation information includes an operation for directing the insertion section 20 toward an extending direction of an insertion object, such as a bending operation, a pushing operation of the insertion section 20, and a pulling operation of the insertion section 20, using an operation section 22. In addition, the recommended insertion operation information includes an operation for rotating the insertion section 20 about the longitudinal axis thereof, such as a twisting operation of the insertion section 20. Furthermore, the recommended insertion operation information includes information on an air supply operation, an air suction operation, and/or a water absorption operation of an interior of an insertion object, using an air supply mechanism, an air suction mechanism and/or a water absorption mechanism. Furthermore, when the insertion section 20 includes a hardness variable mechanism, the recommended insertion operation information may also include a hardness change operation. Furthermore, in an endoscope system, particularly in a large intestine endoscope system, the recommended insertion operation information may include information on insertion operation methods not involved with operating the endoscope system 10, such as a change in the direction of a patient 84 as an insertion object, a procedure for bringing the insertion section 20 under control through the patient 84, etc. The recommended insertion operation determination circuit 86 outputs determined recommended insertion operation information to the state information processing circuit 38 and the recording/playback circuit 88.

Figure 23:
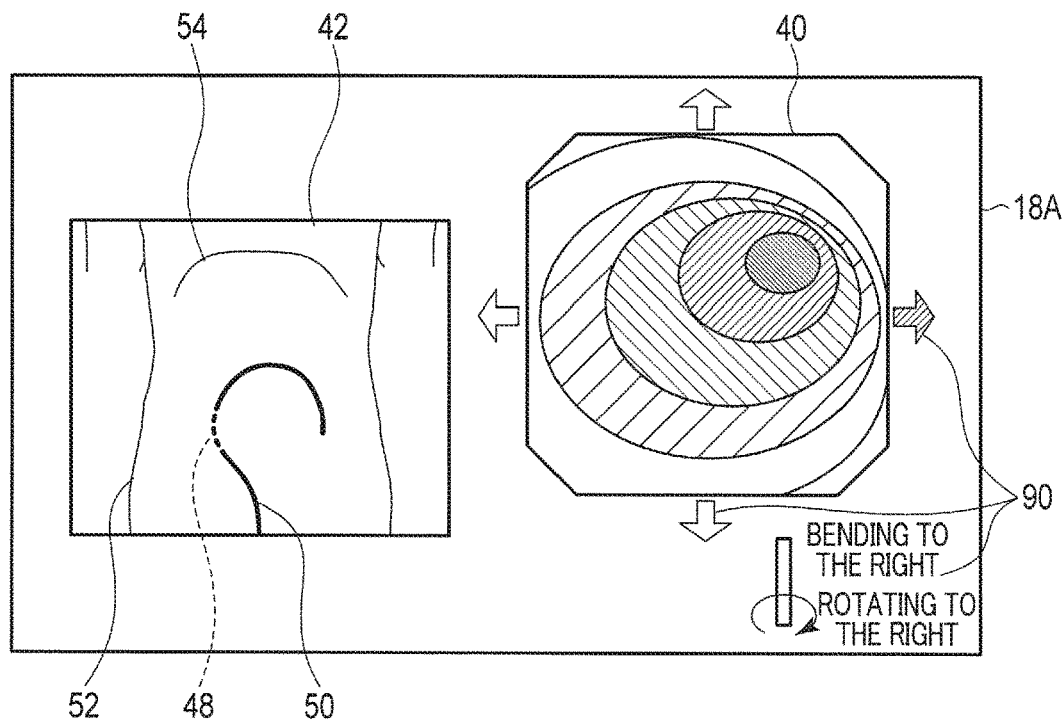
FIG. 23 is a diagram showing an example of a recommended insertion operation information indicator.

The state information processing circuit 38 performs processing for outputting the recommended insertion operation information to an output device. For example, the state information processing circuit 38 performs image processing for displaying recommended insertion operation information on a monitor 18, and outputs the result to the monitor 18. As a result, as shown in FIG. 23, a recommended insertion operation information indicator 90 that presents a recommended operation to the operator 70 by a figure or characters is displayed on a touch panel-equipped display screen 18A of the monitor 18.

Of course, the recommended insertion operation information is not limited to display, and a recommended insertion operation may be output by voice.

The recommended insertion operation information is output in this way, thereby the operator 70 can know a specific operation for proceeding with the insertion or for improving the safety. That is, the insertability and the safety are improved.

A lesion detection circuit 36A detects, as one of the attention state information 48, the presence/absence of a lesion and the position of the lesion, which is attention information about an attention state relating to an insertion object. The lesion detection circuit 36A may be provided separately from the attention state detection circuit 36. The lesion detection circuit 36A detects a lesion by analyzing an image, for example, a video input from an imaging device 26 which is a camera disposed at the distal end of the insertion section 20. In the image analysis, pattern and color matching, machine learning, etc., are used. The lesion detection circuit 36A outputs the detected lesion information to the state information processing circuit 38 and the recording/playback circuit 88.

Figure 24:
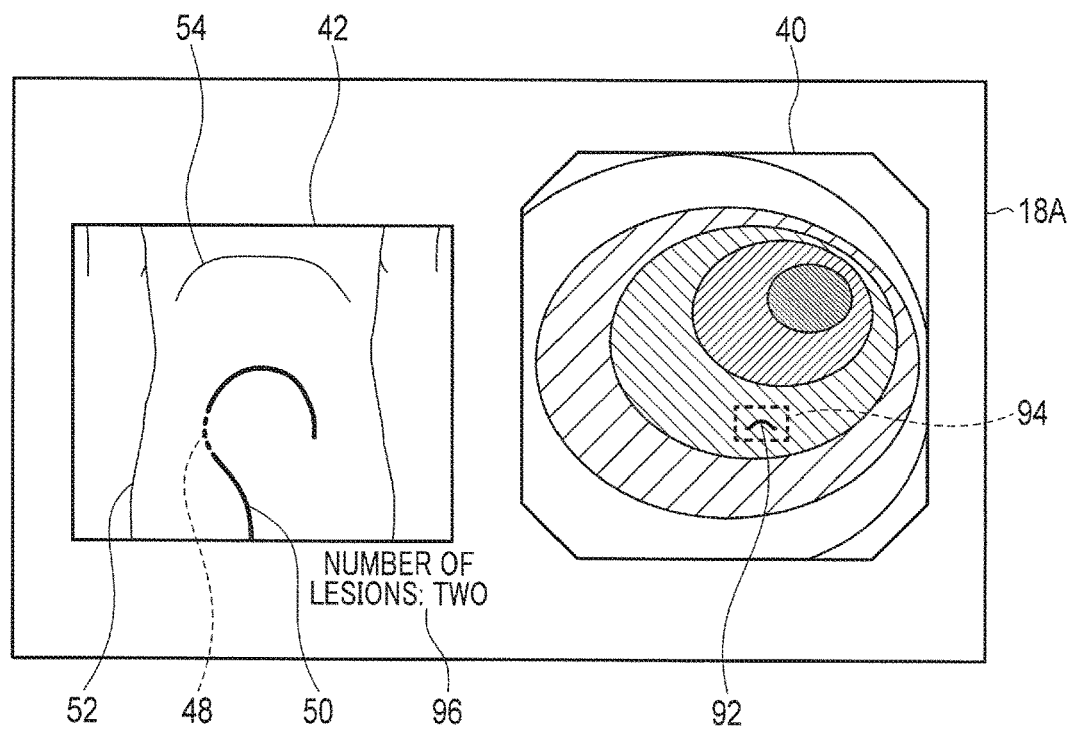
FIG. 24 is a diagram showing an example of a lesion detection result indicator.

The state information processing circuit 38 performs image processing for displaying the lesion information on the monitor 18 which is an output device, and outputs the result to the monitor 18. As a result, as shown in FIG. 24, a lesion detection result indicator 94 that indicates the position of a lesion 92 is displayed on an endoscopic image 40 on a touch panel-equipped display screen 18A of the monitor 18. Furthermore, the state information processing circuit 38 may be configured to count the number of lesions detected by the lesion detection circuit 36A as well as to display a lesion number display (display of the number of lesions) 96.

By thus detecting a lesion or lesions and presenting it or them to the operator 70, an improvement in detection rate of lesions can be expected.

It goes without saying that when the endoscopic image 40 is displayed on the display 80 which is configured to be separate from the monitor 18, the state information processing circuit 38 performs image processing for displaying the lesion information on the display 80 as an output device and outputs the result to the display 80.

The recording/playback circuit 88 includes an unillustrated recording medium and is configured so that at least one of state information detected by the position/calculation unit 34, attention state information detected by the attention state detection circuit 36 (including lesion information detected by the lesion detection circuit 36A), and recommended insertion operation information determined by the recommended insertion operation determination circuit 86 can be recorded and reproduced on the recording medium. In addition, an image acquired at that time may be recorded together with the lesion information. That is, the recording is performed automatically when a lesion is found, whereby the labor of recording performed by the operator 70 and record mistakes can be reduced. The information recorded by the recording/playback circuit 88 can be displayed on the monitor 18 or the display 80 via the state information processing circuit 38.

By recording the attention state information and the recommended insertion operation information in this manner, it becomes possible to analyze data on an endoscopic examination, for example, a cecum arrival rate, a cecum arrival time, an insertion operation in a difficult insertion example, and the data can be used for evaluation of medical quality. Moreover, improving the next endoscopic examination based on the analysis result leads to an improvement of the medical quality.

In addition, by reproducing a recorded difficult-to-insert portion or a recorded lesion position, it is possible to insert the insertion section 20 with care in advance, when the insertion section 20 is inserted into the same patient for the second time and thereafter, and therefore, the insertability, the safety, and the accuracy of medical examinations are improved. Particularly when operators 70 in the first insertion operation and the second insertion operation are different for one patient 84, the operator 70 at the second insertion operation will insert the insertion section into the patient 84 for the first time, but by obtaining information on the insertion from a record on the insertion section inserted once, the insertability, the safety, and the accuracy of medical examination are improved.

Usually, an operator 70 concentrates on insertion when inserting the insertion section 20, and inspects a lesion at the time of extraction of the insertion section 20. By recording the lesion position detected by the lesion detection circuit 36A during insertion and reproducing the positional information of the lesion at the time of extraction, the lesion detected during the insertion can be easily found and inspected at the time of extraction. Furthermore, the possibility of missing, at the time of extraction, the lesion found during the insertion lowers. By doing so, further improvement in detection rate of a lesion or lesions can be expected.

The settings relating to the output of the recommended insertion operation information indicator 90 and the lesion detection result indicator 94 (and/or the lesion number display 96) may also be changed by the operator 70. For example, as shown in FIG. 25, a setting screen relating to the output is displayed on the touch panel-equipped display screen 18A of the monitor 18, and selection of output information is designated by a touch panel as an input interface. In this example, as output information, in addition to the information described in the first embodiment, the recommended insertion operation information indicator 90 and the lesion detection result indicator 94 can be designated as ON/OFF.

A selection designation result by such an input interface is input in the state information processing circuit 38. The state information processing circuit 38 performs processing for outputting the ON-designated output information and supplies the processed output information to an ON-designated output device (e.g., monitor 18, and display 80) to output the processed information therefrom.

As described above, the insertion system according to the second embodiment further includes a recommended insertion operation determination circuit 86 that determines, based on at least one of state information and attention state information, recommended insertion operation information which is a recommended insertion operation method, and a status information processing circuit 38 further performs processing for outputting the recommended insertion operation information to an output device such as the monitor 18.

The recommended insertion operation information is output in this way, so that the operator 70 can know specific operations for proceeding with the insertion or for improving the safety. That is, the insertability and safety are improved.

Alternatively, the insertion system according to the second embodiment further includes a recommended insertion operation determination circuit 86 that determines, based on at least one of state information 50 and attention state information 48, recommended insertion operation information which is a recommended insertion operation method, and a status information processing circuit 38 further performs processing for displaying the recommended insertion operation information to a display 80.

The recommended insertion operation information is output in this way, so that the operator 70 can know specific operations for proceeding with the insertion or for improving the safety. That is, the insertability and safety are improved.

In the present embodiment, the recommended insertion operation information can be at least one of an operation for directing the insertion section 20 toward the extending direction of an insertion object, an operation for rotating the insertion section 20 around the longitudinal axis of the insertion section 20, and an operation of pressing or pulling the insertion section 20.

Thereby, it becomes possible for the operator 70 to know what operation should be performed, from the operation for directing the insertion section 20 toward the extending direction of an insertion object, the operation for rotating the insertion section 20 around the longitudinal axis of the insertion section 20, and the operation of pressing or pulling the insertion section 20.

The insertion system according to the second embodiment may further include a recording/playback circuit 88 which is a recorder capable of recording at least one of the state information and the attention state information.

By recording the attention state information and the recommended insertion operation information in this manner, it becomes possible to analyze data on an endoscopic examination, for example, a cecum arrival rate, a cecum arrival time, an insertion operation in a difficult insertion example and to use the data for evaluation of medical quality. Furthermore, improving the next endoscopic examination based on the analysis result leads to an improvement of medical quality.

Alternatively, the insertion system according to the second embodiment may further include a recording/playback circuit 88 which is a recorder capable of recording at least one of state information, attention state information, and the recommended insertion operation information.

By recording attention state information and recommended insertion operation information in this manner, it becomes possible to analyze data on an endoscopic examination, for example, a cecum arrival rate, a cecum arrival time, or an insertion operation in a difficult insertion example and to use the data for evaluation of medical quality. Furthermore, improving the next endoscopic examination based on the analysis result leads to an improvement of medical quality.

The insertion system according to the second embodiment may further include an input interface, such as a touch panel, a mouse, and a physical switch of a touch panel-equipped display screen 18A of the monitor 18, for designating at least one of attention state information and recommended insertion operation information as ON or OFF, and the state information processing section 38 may be configured to perform processing for outputting at least one of the ON-designated attention state information and recommended insertion operation information, in accordance with the ON designation of at least one of the attention state information and the recommended insertion operation information.

With this configuration, the operator 70 can switch between presence and absence of the output of the attention state information according to the proficiency and preference of the insertion operation of the operator 70.

Herein, when the insertion system is an endoscope system 10, in particular, a large intestine endoscope system, an image as an endoscopic image 40 of the interior of an insertion object captured by the imaging device 26 is displayed on the monitor 18 which is a display device, or if the insertion system further includes a display 80 as a display device, the image is displayed on the display 80, the attention state detection circuit 36 includes a lesion detection circuit 36A that detects a position of a lesion which is an attention state relating to the insertion object from the image captured by the imaging device 26, and the state information processing circuit 38 further performs processing for displaying, on the monitor 18 or display 80, a lesion detection result indicator 94 that indicates lesion positional information on the image captured by the imaging device 26 based on the detection result of the lesion detection circuit 36A.

In this way, by detecting a lesion and presenting it to the operator 70, an improvement in detection rate can be expected.

In this case, the insertion system may further include a recording/playback circuit 88 which is a recorder capable of recording at least one of the state information, the attention state information, and the lesion positional information.

The recording at the time of lesion detection is performed automatically in this way, whereby the labor of recording performed by the operator 70 and record mistakes can be reduced. Furthermore, a lesion position detected by the lesion detection circuit 36A is recorded in the course of insertion of the insertion section 20, and the insertion section is extracted while reproducing the positional information of the lesion at the time of extraction, so that a further improvement in detection rate of the lesion can be expected.

Furthermore, when the insertion system is an endoscope system. 10, in particular, a large intestine endoscope system, the endoscope system may further include a recommended insertion operation determination circuit 86 that determines recommended insertion operation information which is a method of a recommended insertion operation, based on at least one of state information and attention state information; an image as an endoscopic image 40 of the interior of an insertion object captured by the imaging device 26 is displayed on the monitor 18, or if the insertion system further includes a display 80 as a display device, the image is displayed on the display 80; and the status information processing circuit 38 further performs processing for outputting the recommended insertion operation information to the monitor 18 or the display 80, in which the recommended insertion operation information may be at least one of an operation for directing the insertion section 20 toward the extending direction of an insertion object, an operation for rotating the insertion section 20 around the longitudinal axis of the insertion section 20, an operation of pushing or pulling the insertion section 20, a change in orientation of the insertion object, a procedure to suppress the insertion section 20 through the insertion object, and an air supply operation, an air suction operation, and/or a water absorption operation of the interior of the insertion object.

With this configuration, it becomes possible for the operator 70 to know what operation should be performed, from the operation for directing the insertion section 20 toward the extending direction of the insertion object, the operation for rotating the insertion section 20 around the longitudinal axis of the insertion section 20, the operation of pressing or pulling the insertion section 20, the change in orientation of a patient 84 as an insertion object, the procedure to suppress the insertion section 20 through the body of the patient 84, and an air supply operation, an air suction operation, and/or a water absorption operation of the interior of the large intestine lumen of the patient 84.

Third Embodiment

Next, a third embodiment of the present invention will be described. In the following, the same reference numerals are given to the same constituent members as those in the first embodiment, the explanation thereof will be omitted, and only portions different from the first embodiment will be described.

In the first and second embodiments, the position/shape calculation circuit 34 detects state information using a magnetic position detection sensor 16. However, sensors other than the magnetic position detection sensor 16 may be used, as long as they can detect the position and shape of the insertion section 20.

For example, as a sensor detecting the shape of the insertion section 20, a fiber shape sensor can be used, or a plurality of strain sensors can be used in combination. Although a force applied to the intestine is detected from the shape of the insertion section 20, a pressure sensor may be provided in the insertion section 20 to detect the force. Further, by using an imaging device 26 incorporated in the insertion section 20, it is possible to detect the direction of the lumen, the insertion and extraction operation, etc., from the captured image, and to detect the bending shape of the insertion section 20 by using an operation amount sensor provided in the operation section 22.

Figure 26:
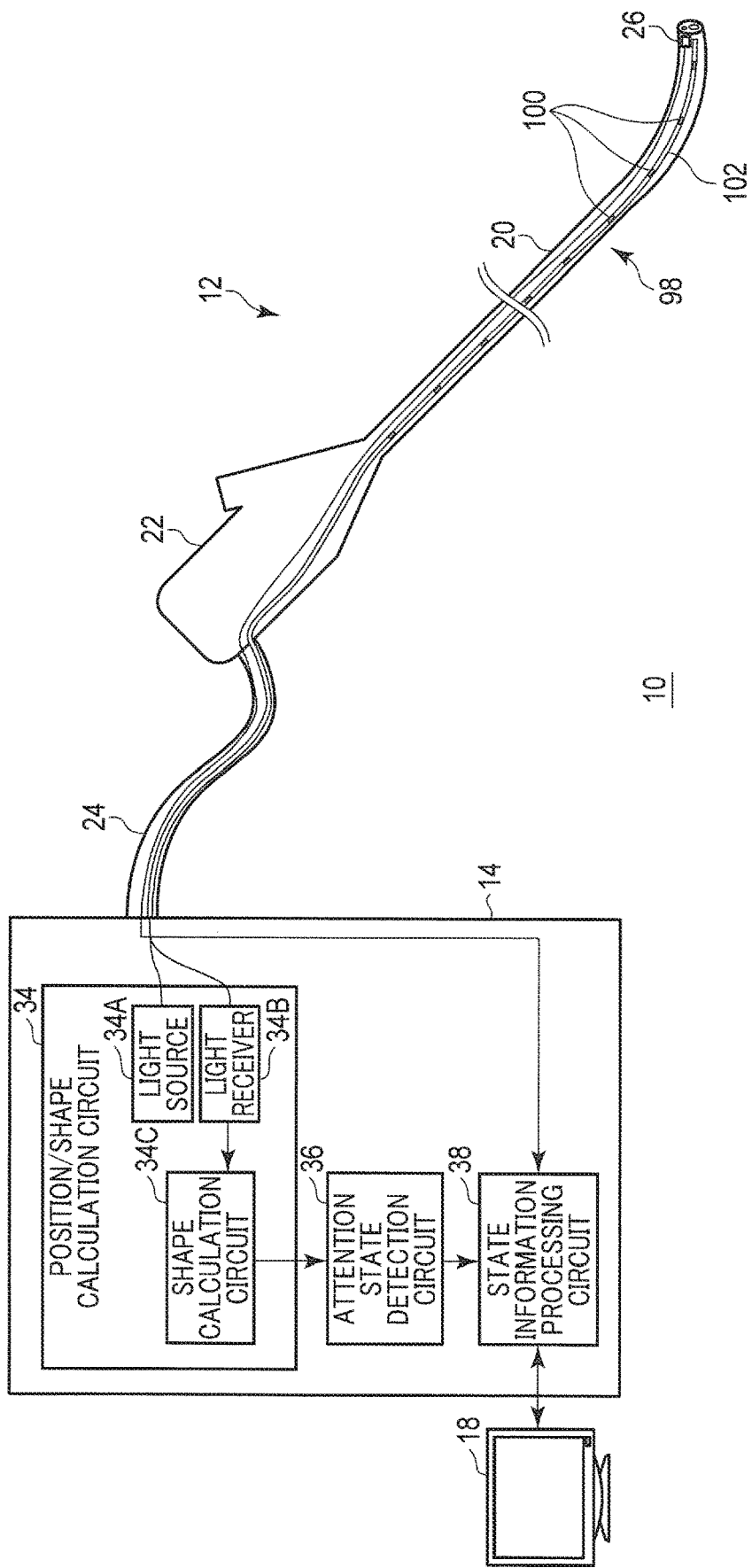
FIG. 26 is a schematic diagram showing the configuration of an endoscope system as an insertion system according to a third embodiment of the present invention.

FIG. 26 is a diagram showing the overall configuration of an endoscope system 10 into which a fiber shape sensor 98 is incorporated. An endoscopic scope 12 including an insertion section 20 and an operation section 22 is connected to an endoscope system main body 14 by a connection cable 24. A position/shape calculation circuit 34 of the endoscope system main body 14 includes a light source 34A, a light receiver 34B, such as a light receiving element, and a shape calculation unit 34C.

As disclosed, for example, in International Publication No. 2015/146712, a fiber shape sensor 98 includes an optical fiber 102 provided with a plurality of detection target portions 100, a light source 34A and a light receiver 34B of a position/shape calculation circuit 34. The detection target portions 100 are arranged in portions where the shape of the insertion section 20 is to be detected. Light emitted from the light source 34A is incident on the optical fiber 102, guided through the optical fiber 102, and returned light that has been reflected by an unillustrated reflector provided at the distal end of the optical fiber 102 and then guided through again the optical fiber 102 is detected by the light receiver 34B.

When the optical fiber 102 is bent according to the bend of the insertion section 20, the detection target portions 100 provided in the optical fiber 102 cause the light guided inside the optical fiber 102 to be emitted outside the optical fiber 102 according to the bending state of the optical fiber 102 or absorb the light. The amount of light emitted outside the optical fiber 102 or absorbed corresponds to the bending amount of the optical fiber 102. The detection target portions 100 are subjected to processing so as to leak light having an amount of light corresponding to the bending amount of the optical fiber 102 to the outside of the optical fiber 102 or to absorb the light. In other words, the detection target portion 100 changes the optical properties, for example, the amount of light, of light guided by the optical fiber 102 according to the bending state of the insertion section 20.

The light receiver 34B receives light incident from the optical fiber 102, and outputs a light reception signal corresponding to the received light amount, etc. That is, the light receiver 34B outputs a light reception signal corresponding to the size (bending amount) of the bend of the insertion section 20 based on the light reception signal.

The shape calculation unit 34C calculates the shape of the insertion section 20 from the bending amount of the insertion section 20 at the position of each of the detection target portions 100 indicated by the light reception signal from the light receiver 34B to obtain shape information. This shape information is output as state information to the attention state detection circuit 36.

Each detection target portion 100 emits broadband light including a plurality of wavelength components from the light source 34A, and emits light rays having a wavelength different from one another to the outside, or absorbs the light rays. Alternatively, light emitted from the light source 34A may be narrow band light such as a laser, and each detection target portion 100 may be the one that performs wavelength conversion to light rays of different wavelengths. With this configuration, in the light receiver 34B and the shape calculation circuit 34C, it is possible to discriminate the light amount change by each of the detection target portions 100.

As described above, in the insertion system according to the third embodiment, the position/shape calculation circuit 34 uses at least one of a fiber shape sensor, an imaging device 26 incorporated into the insertion section 20, a strain sensor, and an operation amount sensor.

As described above, the position/shape calculation circuit 34 can detect state information by using a sensor other than the magnetic position detection sensor 16. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion system comprising:
a processor comprising hardware, wherein the processor is configured to:
determine, for each of a plurality of times, one or more positions of an insertion section configured to be inserted into an insertion subject;
determine, for the each of the plurality of times, a state of the insertion section relative to the insertion subject based on the one or more determined positions of the insertion section;
determine, for the each of the plurality of times, whether an attention state of the insertion section that restricts insertion of the insertion section into the insertion subject has occurred, based on the determined state of the insertion section relative to the insertion subject; and
control a monitor to display attention state information indicating tracks of the one or more positions of the insertion section when the attention state occurs, based on the attention state and the one or more determined positions of the insertion section,
wherein the insertion subject is a tubular structure configured to stretch, and
wherein the processor is further configured to:
determine, for the each of the plurality of times, whether a change in a position of a predetermined portion of the insertion section is at or below a movement threshold;
in response to determining that the change in the position of the predetermined portion of the insertion section is at or below the movement threshold, determine, as the state of the insertion section relative to the insertion subject for the each of the plurality of times, a distance that the predetermined portion of the insertion section is inserted past a predetermined position of the insertion subject;
determine, for the each of the plurality of times, whether the distance exceeds a first threshold; and
in response to determining that the distance exceeds the first threshold, determine, for the each of the plurality of times, that the attention state of the insertion section has occurred.

2. The insertion system according to claim 1,
wherein the processor is configured to:
control the monitor to display the attention state information in a detailed state information display area of the monitor in which the attention state information is displayed by changing at least one of color, characters, figures, and presence or absence of blinking in the one or more positions of the insertion section at which the occurrence of the attention state of the insertion section is determined over the plurality of times.

3. The insertion system according to claim 1,
wherein the processor is configured to:

determine, for the each of the plurality of times, whether the distance exceeds a second threshold less than the first threshold;

in response to determining that the distance exceeds the first threshold, determine, for the each of the plurality of times, that the attention state of the insertion section has occurred and that the insertion subject is in a first degree of extension; and in response to determining that the distance does not exceed the first threshold but exceeds the second threshold, determine, for the each of the plurality of times, that the attention state of the insertion section has occurred and that the insertion subject is in a second degree of extension less than the first degree of extension.

4. The insertion system according to claim 1,
wherein the processor is configured to:
determine, for the each of the plurality of times, a shape of at least a portion of the insertion section based on the one or more positions of the insertion section determined for the each of the plurality of times; and
control the monitor to display:
the shape of the at least the portion of the insertion section with the attention state information indicating the one or more positions of the insertion section at which the occurrence of the attention state of the insertion section is determined over the plurality of times; and
a shape of the insertion subject.

5. The insertion system according to claim 4,
wherein the tubular structure is a part of a human body, and
wherein the processor is configured to:
control the monitor to display:
the shape of the at least the portion of the insertion section with the attention state information indicating the one or more positions of the insertion section at which the occurrence of the attention state of the insertion section is determined over the plurality of times;
the shape of the tubular structure; and
a shape of the human body.

6. The insertion system according to claim 1,
wherein the processor is configured to control the monitor to display an image of an interior of the insertion subject captured by an imaging device.

7. The insertion system according to claim 6,
wherein the processor is configured to control the monitor to display the attention state information by changing at least one of a color, characters, figures, and presence or absence of blinking on or adjacent to the image of the interior of the insertion subject.

8. The insertion system according to claim 1,
wherein the processor is configured to:
determine one or more of a direction and an amount to move the insertion section within the insertion subject based on one or more of the state of the insertion section relative to the insertion subject and the attention state of the insertion section; and
control the monitor to display information on the one or more of the direction and the amount to move the insertion section within the insertion subject.

9. The insertion system according to claim 8,
wherein the one or more of the direction and the amount to move the insertion section within the insertion subject comprises:

one or more of a direction and an amount for inserting the insertion section toward an extending direction of the insertion subject;
one or more of a direction and an amount for rotating the insertion section around a longitudinal axis of the insertion section; and
one or more of a direction and an amount for pressing or pulling the insertion section.

10. The insertion system according to claim 8,
wherein the processor is configured to control a memory to record one or more of information on the state of the insertion section relative to the insertion subject, the attention state information, and information on the one or more of the direction and the amount to move the insertion section.

11. The insertion system according to claim 8,
wherein the processor is configured to:
receive an input from an input device; and
in response to receiving the input, control the monitor to display at least one of the attention state information and the information on the one or more of the direction and the amount to move the insertion section within the insertion subject.

12. The insertion system according to claim 1,
wherein the processor is configured to control a memory to record one or more of information on the state of the insertion section relative to the insertion subject and the attention state information.

13. The insertion system according to claim 1,
wherein the processor is configured to:
receive an input from an input device; and
in response to receiving the input, control the monitor to display the attention state information.

14. The insertion system according to claim 1, further comprising:
an endoscope comprising:
the insertion section; and
an imaging device provided in the insertion section.

15. The insertion system according to claim 14,
wherein the tubular structure is a large intestine comprising a cecum, and
wherein the processor is configured to:
determine whether a portion of the insertion section has been inserted through the large intestine to arrive at the cecum based on one or more of an image captured by the imaging device and the determined state of the insertion section relative to the insertion subject.

16. The insertion system according to claim 14,
wherein the processor is configured to:
process an image captured by the imaging device to identify a lesion in the tubular structure;
determine a position of the lesion based on the one or more positions of the insertion section at one of the plurality of times at which the image is captured by the imaging device; and
control the monitor to display information indicating the determined position of the lesion.

17. The insertion system according to claim 1, further comprising:
wherein the processor is configured to:
receive an image of an interior of the insertion subject captured by an imaging device arranged in the insertion section; and
control the monitor to display:
the image of the interior of the insertion subject;
the attention state information; and an indicator on or adjacent to the image of the interior of the insertion subject, the indicator indicating that the attention state information is being displayed.

18. A method comprising:

determining, for each of a plurality of times, one or more positions of an insertion section configured to be inserted into an insertion subject;

determining, for the each of the plurality of times, a state of the insertion section relative to the insertion subject based on the one or more determined positions of the insertion section;

determining, for the each of the plurality of times, that an attention state of the insertion section that restricts insertion of the insertion section into the insertion subject has occurred, based on the determined state of the insertion section relative to the insertion subject; and controlling a monitor to display attention state information indicating tracks of the one or more positions of the insertion section when the attention state occurs, based on the attention state and the one or more determined positions of the insertion section, wherein the insertion subject is a tubular structure configured to stretch, and wherein the method further comprises:

determining, for the each of the plurality of times, that a change in a position of a predetermined portion of the insertion section is at or below a movement threshold;

in response to determining that the change in the position of the predetermined portion of the insertion section is at or below the movement threshold, determining, as the state of the insertion section relative to the insertion subject for the each of the plurality of times, a distance that the predetermined portion of the insertion section is inserted past a predetermined position of the insertion subject;

determining, for the each of the plurality of times, that the distance exceeds a first threshold; and in response to determining that the distance exceeds the first threshold, determining, for the each of the plurality of times, that the attention state of the insertion section has occurred.

19. A non-transitory computer-readable storage medium configured to store instructions that cause a computer to at least perform:

determining, for each of a plurality of times, one or more positions of an insertion section configured to be inserted into an insertion subject;

determining, for the each of the plurality of times, a state of the insertion section relative to the insertion subject based on the one or more determined positions of the insertion section;

determining, for the each of the plurality of times, whether an attention state of the insertion section that restricts insertion of the insertion section into the insertion subject has occurred, based on the determined state of the insertion section relative to the insertion subject; and controlling a monitor to display attention state information indicating tracks of the one or more positions of the insertion section when the attention state occurs, based on the attention state and the one or more determined positions of the insertion section, wherein the insertion subject is a tubular structure configured to stretch, and wherein the instructions further cause the computer to perform:

determining, for the each of the plurality of times, whether a change in a position of a predetermined portion of the insertion section is at or below a movement threshold;

in response to determining that the change in the position of the predetermined portion of the insertion section is at or below the movement threshold, determining, as the state of the insertion section relative to the insertion subject for the each of the plurality of times, a distance that the predetermined portion of the insertion section is inserted past a predetermined position of the insertion subject;

determining, for the each of the plurality of times, whether the distance exceeds a first threshold; and in response to determining that the distance exceeds the first threshold, determining, for the each of the plurality of times, that the attention state of the insertion section has occurred.

* * * * *